United States Patent
Mansmann

[11] Patent Number: 6,132,468
[45] Date of Patent: Oct. 17, 2000

[54] ARTHROSCOPIC REPLACEMENT OF CARTILAGE USING FLEXIBLE INFLATABLE ENVELOPES

[76] Inventor: Kevin A. Mansmann, 599 Longchamps Dr., Devon, Pa. 19333

[21] Appl. No.: 09/151,252

[22] Filed: Sep. 10, 1998

[51] Int. Cl.$^7$ ..................................................... A61F 2/38
[52] U.S. Cl. ................................. 623/20.16; 623/20.19; 623/20.21; 623/20.31; 623/22.15; 623/23.11; 623/18.11
[58] Field of Search .................... 623/8, 11, 16, 623/17, 18, 20, 22, 13

[56] References Cited

U.S. PATENT DOCUMENTS

| | | |
|---|---|---|
| 3,875,595 | 4/1975 | Froning . |
| 3,927,423 | 12/1975 | Swanson . |
| 4,052,753 | 10/1977 | Dedo . |
| 4,164,794 | 8/1979 | Spector et al. ............................ 623/11 |
| 4,344,193 | 8/1982 | Kenny . |
| 4,756,862 | 7/1988 | Spector et al. ............................ 623/11 |
| 4,772,287 | 9/1988 | Ray et al. ................................. 623/17 |
| 4,839,215 | 6/1989 | Starling et al. ......................... 428/131 |
| 4,895,148 | 1/1990 | Bays et al. . |
| 4,919,667 | 4/1990 | Richmond . |
| 4,924,865 | 5/1990 | Bays et al. . |
| 4,976,715 | 12/1990 | Bays et al. . |
| 5,007,940 | 4/1991 | Berg . |
| 5,041,138 | 8/1991 | Vacanti et al. ............................ 623/10 |
| 5,067,964 | 11/1991 | Richmond et al. . |
| 5,171,244 | 12/1992 | Caspari et al. . |
| 5,263,498 | 11/1993 | Caspari et al. . |

(List continued on next page.)

OTHER PUBLICATIONS

Burg, K.J., et al, "Modulation of surface and bulk properties of biomedical polymers," *Annals N Y Acad Sci* 831: 217–22 (1997).

Chen, F.S., et al, "Chondrocyte transplantation and experimental treatment options for articular cartilage defects," *Amer J Orthopedics* 26: 396–406 (1997).

Hubbell, J.A., "Biomaterials in tissue engineering," *Biotechnology* 13: 565–76 (1995).

Minas, T., et al, "Current concepts in the treatment of articular cartilage defects," *Orthopedics* 20: 525–538 (1997).

Thornhill, T.S., "Cartilage resurfacing: Facts, fictions, and facets," *Orthopedics* 20: 819–820. 1997.

*Primary Examiner*—Mickey Yu
*Assistant Examiner*—Tram A. Nguyen
*Attorney, Agent, or Firm*—Patrick D. Kelly

[57] ABSTRACT

A flexible "scaffold" envelope is disclosed which can be used to replace damaged cartilage in knees, shoulders, or other joints of a mammalian body. Designed for use in arthroscopic surgery, the envelope is sufficiently flexible to allow it to be rolled up or folded and inserted into a knee or other joint via a small skin incision. Before insertion, a segment of damaged cartilage is removed from a bone surface, and the bone surface is prepared, using various tools and alignment guides disclosed herein. After the envelope is inserted into the joint, it is unfolded, positioned properly, and anchored and cemented to a bone surface. After anchoring, the envelope is filled via an inlet tube with a polymeric substance that will set and solidify at body temperature. During filling and setting, the surgeon can manipulate the exterior shape of the scaffold envelope, to ensure that the implant will have a proper final shape after the polymer has cured into fully solidified form. Using these materials and methods, a synthetic replacement can be created for damaged or diseased cartilage, having a smooth surface and a non-rigid stiffness closely resembling natural cartilage. The entire procedure can use minimally invasive tools and methods, to avoid having to cut open and fully expose a joint that is being repaired. Various devices and methods are disclosed to facilitate this procedure, including tools and devices to help ensure proper arthroscopic preparation of large bone surfaces, and proper positioning, alignment, anchoring, and filling of a scaffold envelope.

29 Claims, 8 Drawing Sheets

U.S. PATENT DOCUMENTS

| | | |
|---|---|---|
| 5,304,181 | 4/1994 | Caspari et al. . |
| 5,314,478 | 5/1994 | Oka et al. ................................. 623/16 |
| 5,336,266 | 8/1994 | Caspari et al. . |
| 5,344,459 | 9/1994 | Swartz . |
| 5,358,525 | 10/1994 | Fox et al. . |
| 5,556,429 | 9/1996 | Felt . |
| 5,632,745 | 5/1997 | Schwartz ................................. 606/80 |
| 5,645,597 | 7/1997 | Krapiva ................................. 623/17 |
| 5,769,899 | 6/1998 | Schwartz et al. ........................ 623/16 |
| 5,865,849 | 2/1999 | Stone ........................................ 623/11 |
| 5,888,220 | 3/1999 | Felt et al. . |

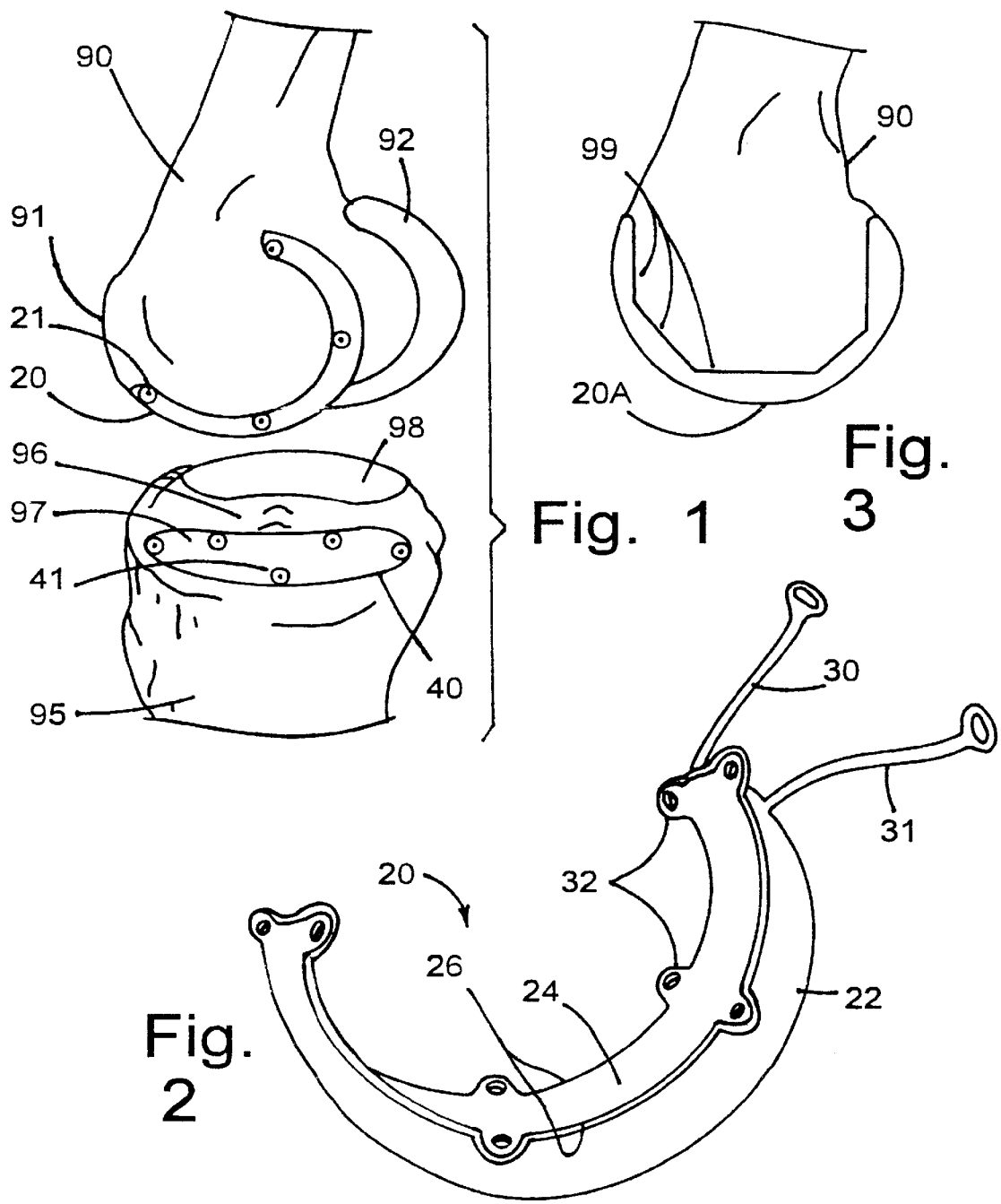

ARTHROSCOPIC REPLACEMENT OF CARTILAGE USING FLEXIBLE INFLATABLE ENVELOPES

BACKGROUND OF THE INVENTION

This invention is in the field of surgery, and more particularly, arthroscopic surgery on joints such as knees, shoulders, or hips. It relates to using arthroscopic devices and methods to replace damaged or diseased cartilage surfaces in mammalian patients.

Cartilage is the type of tissue that coats the ends (or other friction-bearing sites) of various types of bones. It is reasonably hard but not rigid. In a healthy joint, cartilage is characterized by a smooth, slidable surface, to promote comfortable and unhindered movement of the joint; however, in a damaged or diseased joint, the cartilage on one or more bone surfaces may need to be repaired or replaced.

Because of various load-bearing and other physiological factors, the joints that most frequently need surgical repair or replacement are knee joints, hip joints, and shoulder joints; however, other joints (such as finger joints, ankles, etc.) also occasionally need repair, due to injuries, arthritis, and other problems.

To describe and illustrate this invention, the discussion below focuses mainly on knee joints. The initial discussion, which describes and illustrates a relatively simple and basic form of the invention with few enhancements, focuses on a femoral-tibial compartment, i.e., the main load-bearing surfaces between the femur (the thighbone) and the tibia (the shinbone). After that description, various enhancements to this invention are described and illustrated in a patellofemoral interface, since it is easier and clearer to illustrate that simpler part of the knee. However, it should be recognized that the various positioning, anchoring, and other enhancements that are described and illustrated with respect to the patella (the kneecap) can also be adapted if desired to replacing a damaged cartilage segment in a femoral-tibial compartment as well.

In addition, it should be kept in mind that the methods and devices disclosed herein also can be used to repair other types of joints, including shoulder and hip joints. Indeed, because the condyles (i.e., the rounded surface at the end of a bone) in knee joints have complex shapes that are more difficult to work with than the simpler ball-and-socket joints in shoulders or hips, development of this invention to repair complex and difficult knee joints clearly indicates that this invention can be adapted to the simpler joints found in shoulders, hips, and elsewhere.

Various "classical" techniques, tools, and implanted devices that have been used for many years to repair damaged cartilage in knee joints are discussed in medical texts such as *Campbell's Operative Orthopedics,* a five-volume treatise.

Other recent developments, most of which focus on ways of transplanting chondrocyte cells (which generate cartilage) from healthy cartilage into damaged cartilage areas, are described in various articles such as Brittberg 1994, Minas et al 1997, Thornhill 1997, and Chen 1997.

U.S. patents that disclose various types of surgical tools and implantable devices for repairing knee joints can generally be classified into two categories (although, as noted below, these categories have begun to overlap substantially in recent years). The first category, which generally includes older patents, is limited to surgery which requires that the knee must be cut open, to expose at least a portion of the bones that are being worked on, giving the surgeon direct access to the areas being worked on. This type of operation is used in various situations, including: (1) patellar implants, in which a device is inserted to assist a damaged patella (kneecap), as described in U.S. Pat. No. 3,927,423 (Swanson 1975); and, (2) cases that require what surgeons call a "knee replacement" or "total knee replacement" (abbreviated as TKR), in which the ends of the tibia (shinbone) and/or the femur (thighbone) are either cut off or otherwise cut, grinded, or machined to prepare an exposed bone surface, followed by permanently implanting one or more devices on the exposed bone surfaces. Currently, the only TKR devices that have been approved for use in the United States use a metal-surfaced femoral component and a plastic-surfaced tibial component. However, other interfaces have been developed for other joints (including metal-on-metal devices for use in the hip), and research is being done on ceramic replacement joints. Additional patents in the area of "open knee" surgery include U.S. Pat. Nos. 5,171,244 (Caspari et al 1992) and 5,358,525 (Fox et al 1994).

The second major type of approach to repairing knees and other joints is generally referred to as "arthroscopic" surgery. This approach is sometimes called "minimally invasive surgery," but that term is broader and not precise. "Arthroscopic" surgery involves cutting two or more small holes through the patient's skin, near the area to be worked on. A slender light source (usually a flexible fiber optic cable) coupled to a miniaturized lens for a video-type camera are inserted through one hole, so the surgeon can see what he (or she) is doing beneath the skin. One or more tissue manipulating instruments (such as a scalpel blade, a scissors-type cutting device with one or two movable blades, a gripping device such as forceps or a clamp, etc.) are inserted through a second and possibly additional holes. Various patents that disclose instruments or devices that can be used for arthroscopic knee repair or other types of similar surgery (such as laparoscopic surgery) include U.S. Pat. Nos. 4,203,444 (Bonnell 1980), 4,983,179 (Sjostrom 1991), 5,304,181 (Caspari et al 1994), and 5,322,505 (Krause et al, 1994), and numerous other patents as well.

In recent years, the boundary lines between open-knee surgery and minimally-invasive knee surgery have become blurred. For example, various patents issued to Caspari et al (including U.S. Pat. Nos. 5,171,244; 5,263,498; 5,336,266; and 5,395,376) relate to steel-type devices that may be several inches wide or long, which are inserted into the knee through incisions that may also be several inches long. Although this is not truly arthroscopic surgery, it can be called "minimally invasive" surgery, since any incisions that are made through the skin are kept to a minimum size, in view of the needs of the surgery. Accordingly, "minimally invasive surgery" is regarded herein as a much broader and less precise term, which includes both arthroscopic surgery, as defined above, and various other types of surgery in which any incisions through the skin are kept as small as possible. "Minimally invasive surgery" clearly excludes so-called "total knee replacement"; however, nearly any other type of skillful surgery on a knee might be regarded as "minimally invasive", under the broadest implications of the term.

Implantable Meniscus Devices

The current invention relates solely to implantable devices that are securely anchored to a bone surface. As such, it does not relate to items of prior art involving surgical implantation of a "meniscus", which is a peripherally-anchored device that is sometimes implanted in a damaged knee to provide a form of cushion between the femur and tibia bones. Artificial meniscus devices are disclosed in various patents such as U.S. Pat. No. 5,344,459 (Swartz 1994), which discloses a flexible plastic membrane in the shape of a donut or double-donut, with compartments that can be filled with air, a liquid, or a semi-solid after the device has been inserted. To the best of the knowledge and belief of the Applicant (who is a surgeon, specializing in knee surgery), the device disclosed in Swartz's '459 patent is not commercially available, and is not being used by surgeons who perform knee surgery.

Another non-anchored implantable meniscus is disclosed in U.S. Pat. No. 4,344,193 (Kenny 1982), and a somewhat similar non-anchored "spacer" which assertedly can prevent unwanted motion of a kneecap in a damaged knee is described in U.S. Pat. No. 4,052,753 (Dedo 1977).

As mentioned above, these devices are not relevant herein, since the current invention relates to repairing or replacing damaged cartilage. The difficulties and challenges that arise in repairing or replacing cartilage, which requires that any implanted repair device must be permanently and securely anchored to an exposed bone surface, are substantially different from placing a movable device such as a meniscus or spacer inside a joint.

Implantable or Injectable Polymers

Several U.S. patents disclose various types of polymers or proteins that, assertedly, can be injected into a joint as a liquid or semi-liquid composition that subsequently harden into a solidified material.

For example, U.S. Pat. No. 5,556,429 (Felt 1996) discloses injection of a fluidized mixture of a biocompatible polymer (such as a silicone or polyurethane polymer) and a biocompatible "hydrogel" (a hydrophilic polymer, formed by steps such as using an agent such as ethylene dimethacrylate to cross-link a monomer containing a hydroxyalkyl acrylate or methacrylate), into a joint such as the knee, after one or more bone surfaces have been properly prepared. After injection, the polymer and hydrogel mixture can be set into solidified form by means such as ultraviolet radiation, which can be introduced into the subcutaneous area by a fiber optic device. Felt's '429 patent asserts that after the polymer-hydrogel mixture has set, it can be finished and sculpted by means such as using a retractable scalpel with an electrically heated tip that can reach boiling temperature to melt the surface of the polymeric material, thereby allowing it to be sculpted or otherwise modified by the spatula tip. After the heated tip is removed from the polymer surface, the melted surface material will cool again, and will solidify in its newly sculpted form.

That approach may offer promise, but it is not being used by surgeons, and it apparently suffers from several limitations and drawbacks. First, a surgeon's ability to ensure complete and thorough setting of a polymer-hydrogel mixture (especially those portions of the mixture that are directly next to a bone, and thus obscured from direct exposure to ultraviolet light) is limited and uncertain. Second, a surgeon has only limited ability to ensure that the polymerizing fluid, once it sets, becomes securely and permanently anchored to the bone surface.

Concerns over adhesion are highly important, for at least two reason. Most notably, the presence of a hydrogel mixed with the polymer will detract from the adhesive strength of the final polymer. A hydrogel necessarily has a high water content, and the water in the gel cannot and will not adhere to the bone; to put it in simple terms, a hydrogel is included in the mixture in order to make the final material slippery, rather than sticky. In addition, polymeric agents that have been selected for toughness, smoothness, and durability, but which also must provide a substantial amount of non-rigid, non-brittle cushioning in a manner comparable to cartilage, are not likely to also have the characteristics of an ideal adhesive.

Those important limitations, as well as various others, are addressed and overcome by the subject invention disclosed herein.

Additional prior art on surgically implantable polymers is contained in numerous published items; recent review articles include Peppas et al 1994, Hubbell 1995, Stokes 1995, Burg et al 1997, Lewis 1997, Kim and Mooney 1998, and Ambrosio et al 1998. Other discussions of biocompatible implantable materials are also available in various textbooks, such as Silver 1994.

Implants that Promote Cellular Growth

A large amount of research has been carried out on various methods and devices for implanting chondrocyte cells (which generate cartilage, under proper conditions) into damaged knees and other joints. Published articles which discuss such efforts include Brittberg et al 1994, Chen et al 1997, Minas et al 1997, and Thornhill 1997.

Various U.S. patents that are relevant in this field include U.S. Pat. No. 4,919,667 (Richmond 1990), on a multi-layered implant with alternating layers of impermeable plastic to provide smooth sliding surfaces, and porous material to promote ingrowth of cells; U.S. Pat. No. 4,880,429 (Stone 1989), U.S. Pat. No. 5,007,934 (Stone et al 1991), and U.S. Pat. No. 5,306,311 (Stone et al 1994), all of which relate to porous matrices made of natural substances such as collagen, the protein that holds connective tissue together; U.S. Pat. No. 4,846,835 (Grande 1989), which describes techniques for growing chondrocyte cells in vitro, seeding the cells into a collagen matrix, and implanting the matrix and cells in the knee; U.S. Pat. No. 5,041,138 (Vacanti et al 1991), which describes synthetic but biodegradable polymers for use as a matrix material instead of collagen; U.S. Pat. No. 5,206,023 (Hunziker 1993), which discloses a multi-step process for cleaning a cartilage defect and then packing it with material that encourages chondrocyte cells to grow in the repair zone; and U.S. Pat. No. 5,769,899 (Schwartz et al 1998) which discloses a two-component implant which includes a slow-release drug delivery implant that delivers drugs or "repair factors" to a cell-growing implant.

Such efforts to use transplanted chondrocyte cells to regenerate cartilage in a damaged joint suffer from several limitations. Perhaps the most important limitation arises from the fact that under the current state of the art, chondrocyte cell transplants can only be used to repair cartilage defects that are about 1 square centimeter, or smaller, in size. Diligent efforts to work with larger areas have been tried, but the success rates in such efforts drop off sharply when the size of the cartilage defect increases; by the time a defect covers about 2 square centimeters or more, the success rate for chondrocyte-mediated repair is very low. Therefore, repair of a large defect in a cartilage surface of a knee normally requires a "total knee replacement." Accordingly, although chondrocyte transplants are useful for treating many types of sports injuries and other types of mechanical trauma or injury (such as automobile or bicycling accidents, falls, etc.), they are severely limited, and in most cases totally useless, for treating elderly patients, patients suffering from osteoarthritis, and various other types of patients with defects larger than about 1 to about 1.5 square centimeters.

In addition to that size limitation, collagen or other porous proteinaceous matrices disclosed in the patents by Stone, Hunziker, or Grande are not tough and durable, so it is difficult or impossible to anchor them to a bone surface that is subject to loading conditions.

It also should be recognized that repair methods involving transplanted chondrocyte cells under the prior art require long recovery times, compared to other approaches such as a "total knee replacement" using a mechanical joint. Typically, a patient receiving a chondrocyte cell transplant in a knee joint is prohibited from putting any weight on the knee for at least 6 weeks, and many patients are told to not put any weight on the knee for even longer periods, such as 12 weeks. Even after a patient can begin using the knee again, full recovery from chondrocyte cell transplant surgery typically requires numerous months. This type of slow and prolonged recovery period greatly increases the total costs of treatment and recovery (including, in many cases, lost work and lost wages). By contrast, a patient who has a "total knee replacement" (TKR, which involves sawing off and removing a damaged knee joint and replacing the joint with a mechanical device attached to the tibia and femur bones by steel pins) can usually begin to put weight back on the knee within a day or two after the surgery.

The very long recovery period required by chondrocyte cell transplants under the prior art also tends to limit candidate patients to relatively young people who were injured in a sporting event, auto accident, etc. Elderly patients, who are not as active and who will not have to live with a serious knee problem for another 40 years or more, are usually advised to get "total knee replacement" surgery instead.

In summary, chondrocyte cell transplantation is a relatively new technique. Although it holds good promise for some people (especially young people who have suffered an injury rather than a disease), under the current technology, it can only be used to repair cartilage defects that are about 1 square centimeter or smaller in size. Repair of larger defects in a cartilage surface normally requires a mechanical "total knee replacement" rather than a cell implantation procedure.

Accordingly, one object of this invention is to disclose improved methods and devices for replacing damaged cartilage in a knee, using arthroscopic methods, tools, and devices, in a way that eliminates the need for cutting open a knee to provide full exposure of the joint or the cartilage area that needs to be repaired.

Another object of this invention is to disclose a method of arthroscopic surgery on knees or other joints, which is capable of replacing an entire femoral condyle or tibial medial or lateral plateau with a hardened synthetic device, and which thereby overcomes and avoids the size limitation of other repair methods that can only repair a cartilage defect up to 1 square centimeter in size.

Another object of this invention is to disclose a method of arthroscopic surgery on knees or other joints, in which a device is implanted inside the joint, wherein the device provides an immediate and substantial improvement in the condition and operability of the joint, without requiring a delay of weeks or months before weight-bearing or other loads can again be placed on the repaired joint.

Another object of this invention is to disclose a flexible "scaffold" that can be rolled up or folded to allow it to be inserted into a joint through a minimally invasive incision, after a piece of damaged cartilage has been removed. Once the scaffold has been inserted into the joint, it can restored to its original shape, anchored to a bone surface, then filled with a polymer that will harden inside the scaffold, to create a polymeric replacement for damaged cartilage that can be implanted via an arthroscopic incision regardless of the size or surface area of the final implanted device.

Another object of this invention is to disclose a method of using a flexible scaffolding device which, using arthroscopic surgical tools, can be inserted into a diseased or damaged joint such as a knee, properly positioned over a bone surface from which the cartilage has been removed, anchored permanently to the bone surface, and then filled with a curable polymer.

These and other objects of the invention will become more apparent through the following summary, drawings, and description of the preferred embodiments.

SUMMARY OF THE INVENTION

A flexible "scaffold" envelope is disclosed, which can be used to replace damaged cartilage in knees, shoulders, or other joints of a mammalian body. Designed for use in arthroscopic surgery, the envelope is sufficiently flexible to allow it to be rolled up or folded and inserted into a knee or other joint via a small skin incision. Before insertion, a segment of damaged cartilage is removed from a bone surface, and the bone surface is prepared, using various tools and alignment guides disclosed herein. After the envelope is inserted into the joint, it is unfolded, positioned properly, and anchored and cemented to a bone surface. After anchoring, the envelope is filled via an inlet tube with a polymeric substance that will set and solifidy at body temperature. During filling and setting, the surgeon can manipulate the exterior shape of the scaffold envelope, to ensure that the implant will have a proper final shape after the polymer has cured into fully solidified form. Using these materials and methods, a synthetic replacement can be created for damaged or diseased cartilage, having a smooth surface and a non-rigid stiffness closely resembling natural cartilage. The entire procedure can use minimally invasive tools and methods, to avoid having to cut open and fully expose a joint that is being repaired. Various devices and methods are disclosed to facilitate this procedure, including tools and devices to help ensure proper arthroscopic preparation of large bone surfaces, and proper positioning, alignment, anchoring, and filling of a scaffold envelope.

Closed (Synthetic) V. Open (Biological) Scaffolds

It should be noted that two different types of flexible scaffolds, either of which can be inserted arthroscopically into a joint, are envisioned herein. However, only one of these types is covered by this patent application; the other type is covered in a separate co-pending application.

The type of scaffold covered herein is a closed envelope, made of two synthetic layers that are molded or sealed together around their periphery. This type of envelope is essentially watertight (except for an inlet tube, and possibly an outlet tube). This type of closed envelope is designed to be permanently anchored onto a prepared bone surface from which the native cartilage has been removed. After it has been permanently anchored to the bone, it is filled with an injectable polymeric substance that will harden and set to form a non-rigid device that is completely synthetic.

This type of synthetic envelope provides a method of replacing an entire damaged segment of cartilage in a single operation, without requiring a prolonged healing and recovery period while implanted chondrocyte cells grow in situ and generate new cartilage. Accordingly, although these synthetic envelopes can be designed to interact in various ways with chondrocytes or other cells in a repaired joint, these envelopes typically will not require any ingrowth or supplementation by chondrocytes or other cells.

The other type of joint repair scaffold is mentioned herein only in passing, for completeness; it is discussed in detail and claimed in a separate co-pending patent application. It involves an open-type scaffold which uses "runners" to both: (i) subdivide a large cartilage defect into smaller zones, called scaffold compartments; and, (ii) provide load-sharing support for the repaired surface while the chondrocyte cells generate new cartilage. Using this approach, each compartment created by the runners in the scaffold provides a relatively small, protected and sheltered environment for transplanted chondrocyte cells. In this manner, the size of cartilage defects that can be repaired using transplanted chondrocyte cells can be substantially increased, compared to the current size limitation of about 1 square centimeter under the prior art.

As noted above, open-type scaffolds with runners, designed for enlarging and promoting biological regeneration of cartilage, are covered in a separate application. They are not discussed in any detail herein. This current application relates solely to "closed envelope" scaffolds which are designed to provide a synthetic replacement for damaged cartilage, rather than a cell-generated biological repair that requires weeks or months of recovery.

BRIEF DESCRIPTION OF THE DRAWINGS

FIG. 1 illustrates the arrangement of the femur (thighbone) and tibia (shinbone) in a knee, showing the two rounded parallel femoral condyles, and the two concave tibial plateaus, which are separated by the tibial spine. In a uni-compartmental repair, one femoral condyles has been covered by a femoral scaffold, and the corresponding tibial plateau has been covered by a tibial scaffold.

FIG. 2 is an oblique view showing a femoral scaffold envelope, designed to be placed on the convex surface of a single femoral condyle (medial or lateral). This envelope has a smooth-curved (rather than faceted) anchoring surface.

FIG. 3 is a side view showing how a femoral scaffold envelope with a faceted anchoring surface will interact with a femoral condyle surface that has been prepared by a grinding operation to have complementary facets.

DESCRIPTION OF THE PREFERRED EMBODIMENTS

Figure 4:
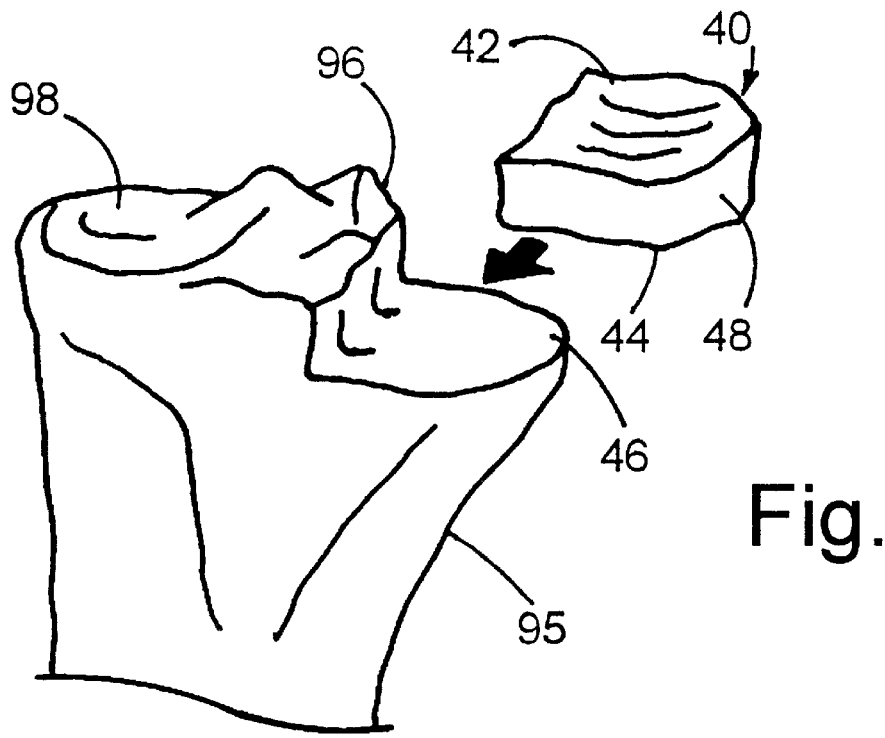
FIG. 4 illustrates how a tibial plateau is prepared, by a grinding operation, to have a flat horizontal platform which will accommodate a tibial scaffold envelope with a flat anchoring membrane and a concave articulating membrane.

For purposes of explanation and illustration, the initial discussion below focuses mainly on arthroscopic implantation of two inflatable scaffolding devices, to replace damaged cartilage segments on the load-bearing interface between a femur (thighbone) and tibia (shinbone). One scaffold will create a convex layer for a femoral condyle; the other scaffold will create a concave layer for a tibial plateau.

Following that discussion, various options and enhancements are described and illustrated in a discussion of a patellar (kneecap) implant. Those options and enhancements are covered in the patellar analysis, because they are easier to illustrate in that context; however, they are also feasible in femoral and/or tibial implants.

As is well-known to those skilled in the art, and as shown in a simplified manner in FIG. 1, the lower end of femur 90 (in layman's terms, the "thighbone"), has two convex rounded segments, shown as structures 91 and 92 in FIG. 1. These are the two femoral condyles. The "medial" condyle 91 is on the inner side of the leg, while the "lateral" condyle 92 is on the outer side of the leg. These two femoral condyles are generally parallel to each other, in a configuration that is comparable to the two rims of a pulley.

The two femoral condyles in a knee joint interact with a complementary surface (called the tibial plateau) on the upper end of tibia 95 (the shinbone). Rather than being a simple concave surface, the tibial plateau has a raised promontory 96 in its center with two small peaks, called the "tibial spine". This tibial spine 96 helps create and define two concave surfaces, shown as bone surfaces 97 and 98 in FIG. 1, on both sides of the tibial spine 96. These two concave structures are the medial tibial plateau 97, on the inner side of the leg, and the lateral tibial plateau 98, on the outside of the leg. These are also referred to simply as the medial plateau, and the lateral plateau.

The structures and arrangement of the femoral and tibial surfaces helps stabilize the knee while permitting normal motion. When a knee is repeatedly bent and straightened, such as during walking or running, the two femoral condyles slide and roll back and forth in the medial and lateral tibial plateaus, on opposite sides of the tibial spine. When a person stands or engages in various other activities, this arrangement also gives the knee a substantial amount of rotational movement, allowing the person to move his feet slightly outward in a manner that offers better stability for standing and similar actions.

To simplify and clarify this analysis, the description below describes replacement of cartilage covering a single femoral condyle (either medial or lateral), and a single tibial plateau. After the implant procedure has been completed, the two scaffolds will press and slide against each other as "articulating" surfaces in the patient's knee. This type of repair, often referred to as "uni-compartmental" repair, is fairly common, since a damaged and irregular surface on either of two articulating surfaces often inflicts damage on the surface it rubs against, inside the knee.

If necessary, both femoral condyles and/or both tibial plateaus in a single knee can be resurfaced using scaffold envelopes as disclosed herein, either in a single arthroscopic procedure, or in a series of two such procedures on different days. In one preferred embodiment, a "bi-compartmental" operation would simply repeat the steps described herein, on both the medial (inner) and lateral (outer) sides of a single knee, using two different scaffolds, each of which covers a single (medial or lateral, but not both) femoral condyle or tibial plateau.

In an alternate preferred embodiment, a substantially larger femoral scaffold can be used which will generally have a "U" or horseshoe shape, which can handle both the medial and lateral condyles with a single scaffold envelope. This type of envelope can be provided with separate compartments for the two condyles, if desired. In addition, a single device (with multiple compartments, if desired, can also cover the patellar-facing surface of the femur as well, by means of a scaffold extension which will extend in an upward direction, on the anterior surface of the femur, once it is anchored to that femoral surface.

Similarly, a U-shaped tibial plateau implant can also be used, which will cover both the medial and lateral components of a tibial plateau, and which will generally circumscribe the tibial spine, in the center, which is not covered by cartilage.

Alternately, depending on the condition of the cartilage surfaces in a knee, it may be necessary to resurface only a single femoral condyle, or a single tibial plateau; or, it may be necessary to resurface both femoral condyles (medial and lateral) without resurfacing the tibial plateaus, or vice-versa.

Accordingly, referring to the drawings, callout number 20 in FIG. 2 (and in various other figures) refers to a femoral scaffold envelope, designed to be placed on the convex surface of a single femoral condyle (medial or lateral). Callout number 40 in FIG. 1 refers to a tibial scaffold envelope, which will have a similar structure and function as a femoral scaffold 20, but with a somewhat different external shape.

Both of these inflatable scaffold envelopes (femoral scaffold 20 and tibial scaffold 40) are referred to interchangeably as scaffolds or envelopes. Any reference in the text or claims herein to a scaffold or envelope is limited to a device which has each and all of the following characteristics: (i) the device must be designed for arthroscopic insertion and implantation into a mammalian joint, such as a knee, hip, shoulder, etc; (ii) it must be flexible, in a way that renders it suitable for surgical implantation through a minimally-invasive incision through a patient's skin; (iii) after the device has been inserted into a joint via a minimally-invasive incision, the device must be capable of being restored to a desired size and shape that is useful for replacing a segment of damaged or diseased cartilage in the joint; (iv) the device must have an envelope-type structure that allows it to be anchored to a bone surface in a relatively flat "unfilled" configuration, and subsequently filled with a hard-setting compound that will cause the resulting implanted device to provide a medically effective replacement for a damaged or diseased segment of cartilage; and, (v) it must be manufactured, packaged, and handled in a medically acceptable and sterile manner, to render it suitable for surgical implantation inside a mammalian joint.

As used herein, "arthroscopic" and "surgical" are used interchangeably. These are surgical implants, since they are implanted inside a joint by means that include cutting and physical manipulation of skin, tissue, and bone. These devices are also "arthroscopic" devices, which are intended to be implanted in a joint by means of minimally-invasive techniques, assisted by the use of arthroscopes to allow the surgeon to see what is being done inside a joint, beneath the skin. If desired, these devices disclosed can also be implanted into a joint by means of "open knee" surgical techniques, without using arthroscopic methods or devices. For example, if a joint suffering from multiple or disseminated damage has been opened up using classical techniques, one or more damaged segments of cartilage can be replaced using the same types of scaffold envelopes disclosed herein.

Femoral scaffold envelope 20 has an articulating membrane 22 (also called outer membrane 22) and also a anchoring membrane 24 (also called bone membrane 24). These terms refer to the positioning of a membrane after the device has been anchored to the end of a bone. An anchoring (bone) membrane will be pressed against a bone surface, while articulating (outer) membrane will provide an exposed articulating surface.

As shown in FIG. 4, tibial scaffold envelope 40 also has an articulating (outer) membrane 42, and an anchoring (bone) membrane 44. A preferred method for preparing a tibial anchoring surface 46 comprises grinding a portion of the tibial plateau off in a relatively flat and planar shape while sparing the raised tibial spine 96, to create anchoring surface 46. To accommodate that approach, which slightly reduces the height of the tibia bone 95 in the prepared area, tibial scaffold 40 is generally thicker than a femoral scaffold, and includes a vertical wall or rim portion 48, between the exposed articulating membrane 42 and the anchoring membrane 44. Except for those differences, any comments concerning the design and fabrication a femoral scaffold envelope also generally apply to a tibial scaffold envelope.

Femoral scaffolds can be designed with either curved or faceted anchoring surfaces. If a femoral bone is prepared in a rounded manner, as described below, the scaffold envelope should have an accommodating curved anchoring surface, as shown in FIG. 2. Alternately, if a bone surface is prepared in a faceted manner, with a plurality of flat faces 99 at controlled angles, the scaffold envelope 20A should have an accommodating faceted anchoring surface, as indicated by FIG. 3.

In a preferred embodiment, a tibial scaffold can have a flat anchoring surface, designed to lie securely against a flat and horizontal tibial bone surface, as illustrated in FIG. 4.

In femoral scaffold envelope 20, as shown in FIG. 2, exposed membrane 22 and anchoring membrane 24 are sealed together around their entire periphery by a watertight seam 26, except for an inlet orifice connected to inlet tube 30 and an optional outlet orifice connected to optional outlet tube 31. The watertight seam 26 that couples membranes 22 and 24 to each other can be created by any suitable means (such as molding or heat-sealing) during the envelope manufacturing process.

The combination of a watertight seam 26 and inlet tube 30 allows a fluidized chemical compound or mixture (such as an epoxy, resin, or other polymeric or pre-polymeric compound or mixture) to be injected into the scaffold envelope 20, in a way that causes the compound or mixture to remain inside the envelope 20 without escaping in a manner that would contaminate the joint with unwanted material or debris.

For convenience, terms such as "polymeric mixture" or "polymeric substance" are used to refer to a compound or mixture which is injectable in a fluidized form, and which, after being injected into a scaffold envelope, will set and solidify into a final polymer having a desired stiffness and preferably non-rigid resilience. A polymeric mixture having these traits typically will contain at least one type of monomeric or other relatively small molecular building block, at least one type of chemical crosslinking agent, and if desired, an additional reagent to help ensure that the resulting polymer has a desired average chain length and desired levels of crosslinking and side-chains, to help ensure that the final polymer has the desired physical and mechanical traits after it has solidified, resembling the natural properties of cartilage.

If desired, an optional outlet tube 31 can also be provided, to ensure that little or no air, inert gas, or other liquid or fluid remains entrapped inside the envelope, after the polymer has been injected into it. If an outlet tube 31 is used, one or more internal runners (discussed below) can be positioned inside the envelope in a manner that cause the runner(s) to act as baffles, to direct the movement of the polymer through the envelope along a single flow channel that leads from the inlet tube 30 to the outlet tube 31. This use of a baffle to create a single flow channel for the polymeric mixture will minimize the creation of any unfilled pockets of inert gas, saline solution, etc. If an outlet tube is not provided, the entire scaffold envelope 20 and inlet tube 30 can be packaged in a sealed airtight plastic wrapper, under vacuum conditions, to ensure that only very tiny quantities of a physiologically acceptable gas or liquid remain inside the scaffold envelope when it is implanted in a joint.

Figure 15:
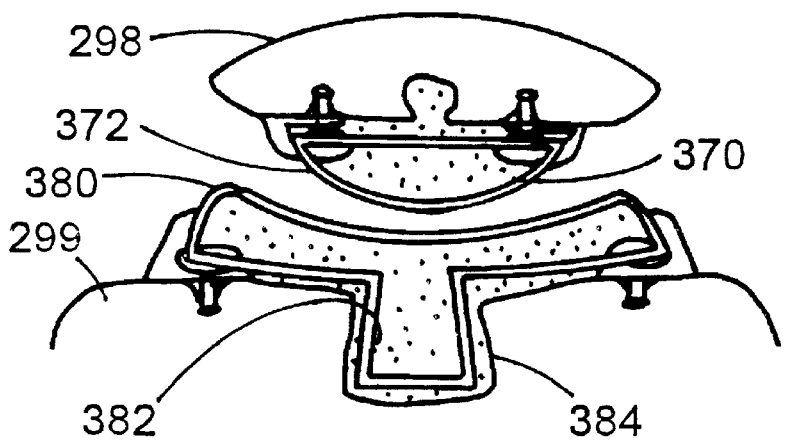
FIG. 15 is a cross-section of patello-femoral implants, with the articulating surface of the patellar scaffold coated by a metallic layer, and wherein the femoral implant has a keel structure that extends downward and fits into a groove created in the bone surface, for greater strength and stability.

To help ensure proper filling of a scaffold envelope, it can be divided into several compartments, each having its own inlet tube (and optional outlet tube, if desired). For example, a scaffold envelope can use a "keel" structure that will extend below or beyond the anchoring face of the envelope, as illustrated in FIG. 15 for a patello-femoral joint, discussed below. This keel structure will fit into a groove that has been machined in the bone, to provide added stability and strength to the implant. If this approach is used, the keel structure can be a separate sealed compartment within the scaffold envelope, which can be filled with a polymeric mixture before the main body of the envelope is filled. This will allow the surgeon to ensure that the anchoring membrane of the scaffold envelope is properly settled into (and cemented onto) the correct position on the prepared bone surface, before the main chamber of the envelope is filled. In a second filling step, a second chamber comprising a rim structure, which surrounds the periphery of the scaffold envelope, can be filled, and adjusted as necessary for proper placement. In a separate third filling step, the center (and primary load-bearing) portion of the scaffold envelope can be filled with the polymeric mixture.

After the polymeric mixture has been injected into envelope 20, it will set (harden) into its final shape, inside the scaffold envelope. The resulting combination of a flexible polymeric envelope, which contains and covers a hardened non-rigid polymer, will provide a smooth-surfaced, non-brittle, medically effective replacement for a segment of damaged or diseased cartilage.

In one preferred embodiment, femoral scaffold envelope 20 is also provided with a plurality of anchoring tabs 32, at spaced locations around the periphery of envelope 20, as shown in FIG. 2. Each tab is designed to accommodate a single anchoring pin that will be driven into the bone. Various types of bone-anchoring pins have been developed for other purposes, and are commercially available from various companies such as Mitek and Suretac.

Alternately, anchoring holes can be provided inside the rim of a scaffold, by means such as molded holes and recessed surface rings to accommodate the heads of anchor pins or other anchoring devices. This is shown by the internal placement of anchors 21 and 41 in femoral and tibial scaffolds 20 and 40.

In addition to using pin-type anchors to secure a scaffold envelope to a bone, the anchoring membrane 24 can also be cemented directly to a bone surface that has been prepared as described below, using a suitable cement such as a polymethylmethacrylate.

As used herein, phrases such as "permanently anchored to a bone surface" do not require use of anchoring pins, staples, or similar devices that penetrate a bone surface. For example, in frail and elderly patients suffering from osteoporosis or certain types of arthritis, it may be preferable to eliminate any anchoring pins or other devices that would penetrate a weakened bone surface. This would avoid or minimize the creation of additional holes in or other damage to the underlying bones. In such cases, use of a strong and non-resorbing cement which is selected and intended to create a permanent bond between a scaffold envelope and a bone surface is regarded herein as an alternate method of anchoring a scaffold envelope to the bone.

In addition, indirect means of anchoring a scaffold to a bone can also be used to permanently anchor a scaffold envelope to a bone surface. Examples of this approach, in which scaffold envelopes are cemented to anchored "positioning rings", are discussed below and illustrated in FIGS. 14 and 15.

Stabilizing Platform and Machining Tools

Figure 5:
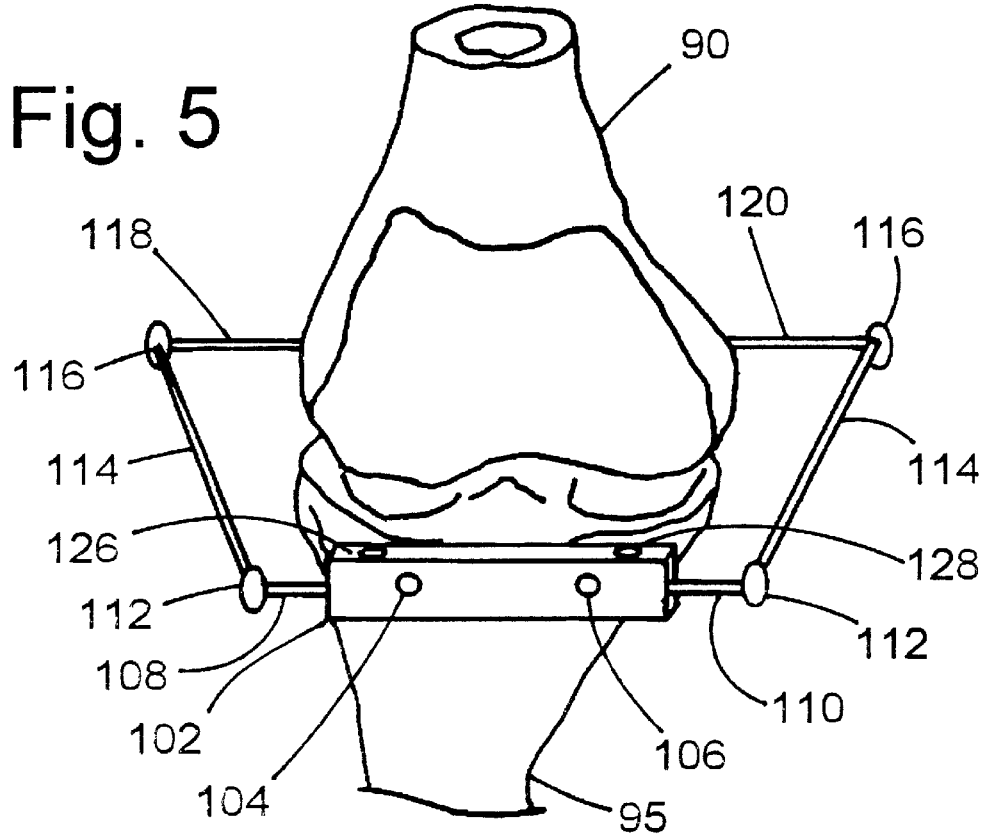
FIG. 5 depicts a stabilizing platform that is affixed to the tibia bone via pins, and which is also coupled to the femur bone via cammed hinges, to ensure proper alignment of the femur and tibia at all stages of flexion and extension of the knee.

After a patient's leg has been anesthetized (such operations usually will not require general anesthesia), a device to assist in proper alignment and in the grinding, polishing, and other arthroscopic and surgical work, is secured to the patient's femur and tibia bones. An assembly 100 for doing this type of work is shown in FIG. 5.

In one preferred method of attachment, stabilizing platform 102 has two tibial pins 104 and 106, which emerge from the proximal surface of platform 102 (i.e., the surface that is closest to the knee, when the platform is in place). After the patient's leg has been anesthetized, these two tibial pins 104 and 106 are driven through the skin on the front of the knee, below the joint line, and into the proximal surface of tibia (shinbone) 95.

This type of tibial platform, by itself, was developed for "total knee replacement" (TKR) surgery, and is widely used by knee surgeons. However, the additional components disclosed below, including the cam-hinged femoral attachments, are believed to be new; accordingly, this type of hinged knee alignment platform, with a fixed tibial attachment and a cam-hinged femoral attachment, is believed to be a new and useful invention in its own right. Because the claims are patentably distinct, the scaffold envelopes disclosed herein are claimed in one patent application, while the aligning devices are claimed in a separate simultaneously-filed application.

Two extension prongs 108 and 110 emerge from the lateral ends of tibial platform 102. These two extension prongs 108 and 112 are coupled, via two tibial hinges 112, to extensions 114, which are also coupled at their other ends to two femoral hinges 116. The two femoral hinges 116 are coupled to the two ends 118 and 120 of a metallic pin that has been driven through the femur bone 98, via incisions on both sides of the femur. Because of the cammed hinges, discussed below, this metallic pin, when emplaced directly through the femur, can interact with the other components of the alignment device to provide precise and reliable mechanical and anatomic alignment of the femur and tibia, even as the knee is flexed and extended. Accordingly, these devices can help a surgeon correct various problems that may be related to the patient's condition, such as a form of bow-leggedness that often results from arthritic damage to the knees.

This platform-securing procedure can be done while the patient's leg is kept straight, such as while the patient is lying horizontally on an operating table. The patient's knee is then bent, usually by lowering a segment of the operating table, so that the patient's calf and tibia are lowered into a vertical position, pointing downward, while the thigh and the femur bone remain horizontal. This movement of the knee joint and tibia allows access to the femoral condyles and the tibial plateaus, in the manner shown in the drawings. As the calf and tibia are being moved downward to a vertical position, the tibial hinges 112 and femoral hinges 116 rotate. This hinged mechanism allows platform 102 to remain directly in front of tibia 95, firmly attached to it via the two frontal tibia pins 104 and 106.

Tibial platform 102 contains at least two coupling receptacles (or other coupling devices) 126 and 128, mounted or positioned on the upper surface of platform 102, as shown. These coupling means 126 and 128 are provided with connecting mechanisms (such as slotted holes or "bayonet" fittings), which can be used to temporarily but securely mount various devices (such as a "slotted burr guide" 140, discussed below) on top of platform 102. This arrangement allows a variety of interchangeable slotted burr guides and other devices and tools to be used during the arthroscopic procedure, to assist the surgeon while he works on the knee.

Preparing Bone Surfaces

Before a flexible scaffold envelope as disclosed herein can be placed and anchored on a femoral condyle or tibial plateau, the bone surface that will be covered by the implant needs to be properly prepared. Typically, this will require (i) removal of any native cartilage from the femoral condyle or tibial plateau surface, so the implant can be anchored securely and permanently, without interference by a damaged or diseased segment of cartilage, and (ii) grinding and levelling the exposed bone surface to a properly shaped, relatively smooth surface, so that the weight of the patient's body, when placed on the patient's leg, will be properly distributed across the implant surface as the patient stands, walks, or engages in other activities after the knee has healed.

If the bone surface and the exposed implant surface are not properly shaped and machined during the arthroscopic procedure, the patient is likely to suffer from chronic or acute discomfort during walking or other activities, if the patient's entire weight comes to rest on an undesired protrusion inside the knee; this would be similar to the discomfort someone feels when walking on a heel with a bone spur. In addition, improper loading can cause or accelerate loosening of or other damage to the implant. Accordingly, proper preparation of the exposed bone surface where the implant will be positioned is essential to proper use of this invention.

As noted above, platform 102 (which is securely affixed to the tibial bone) has coupling receptacles or devices 126 and 128, mounted or positioned on the top surface of platform 102. These coupling means 126 and 128 allow an interchangeable "slotted burr guide" 140 and various other devices to be used during an arthroscopic procedure, to assist the surgeon.

Figure 6:
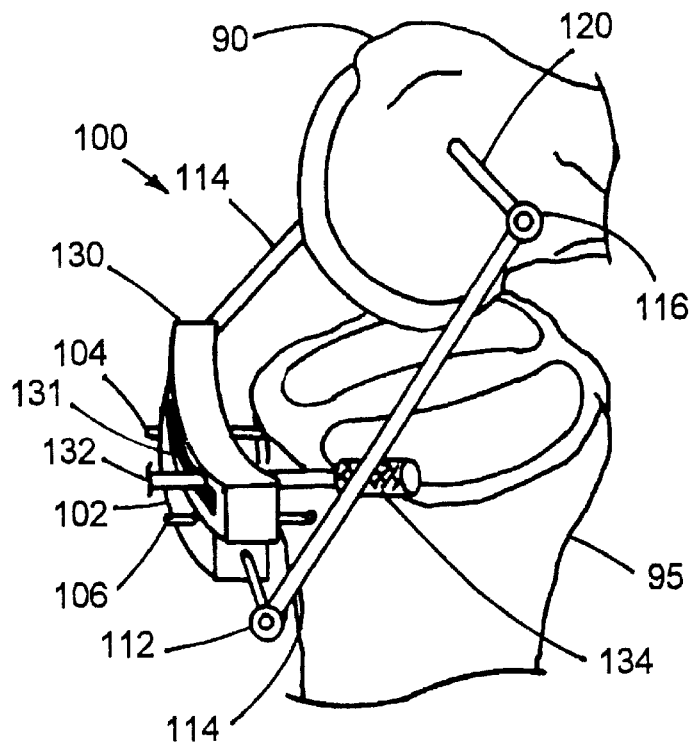
FIG. 6 depicts a grinding burr mounted at the end of a shaft sleeve, for use in removing cartilage and preparing a bone surface for a scaffold implant. The grinding tool passes through an aligning and stabilizing guide that is temporarily affixed to the platform mounted on the tibia bone.

A high-speed rotating tool can be used to remove cartilage and prepare a bone surface for an implant. A simplified depiction of the operating end of a grinding or polishing tool 150 is shown in FIG. 6, with shaft sleeve 152, and burr 154 mounted at the end of an internal rotating shaft inside shaft sleeve 154.

These grinding tools are somewhat similar to a dentist's drill having interchangeable heads. The burrs, which have a variety of sizes and shapes, are usually made of very hard metal, and have a grooved, abrasive, or other surface that is suited for grinding, polishing, or similar use. The shaft has both an outer sleeve, which does not rotate, and an inner shaft that can rotate at relatively high speeds. The sleeve provided by the outer shaft also provides a means for suction removal of debris generated by a grinding operation.

These devices are commercially available from companies such as Dyonics, Arthrotek, and Arthrex, and are widely used in conventional arthroscopic procedures. Typically, burr-and-shaft assemblies that are roughly 20 cm long (about 8 inches) are used with a driving machine that has a hinged and movable arm. A fitting at the end of the arm allows various burr and shaft assemblies to be quickly connected to or disconnected from the machine arm, as needed. Because of the risk of clogging by bone chips and other debris, most burr heads used in arthroscopic procedures are disposable, and are discarded after an operation is completed.

Figure 7:
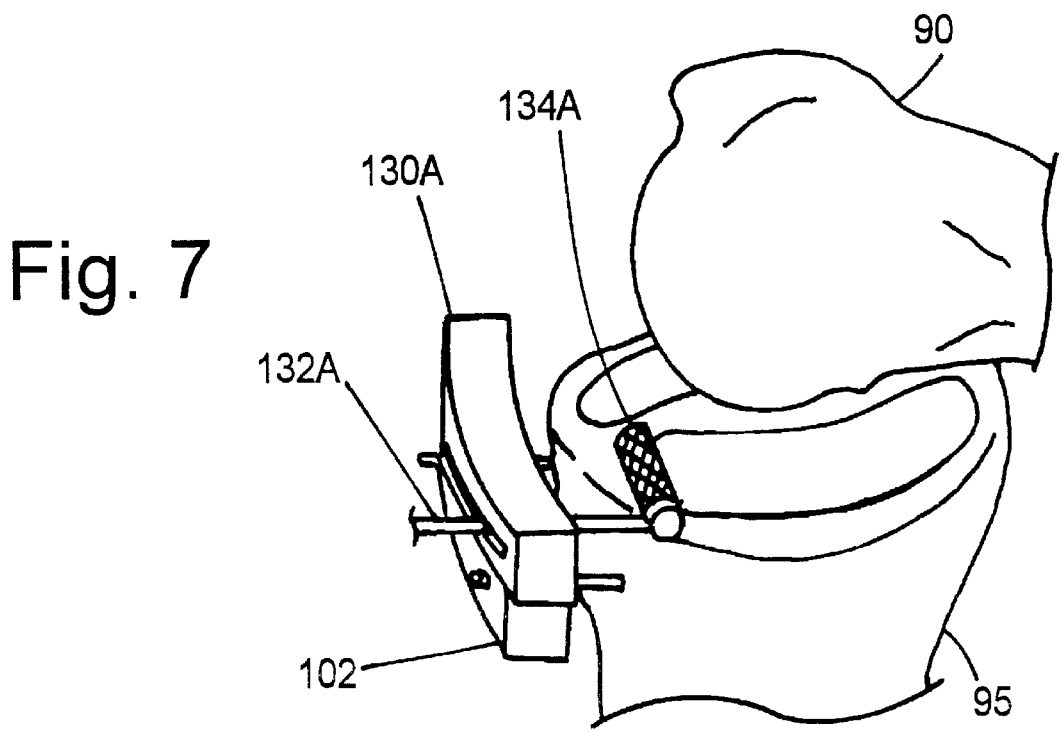
FIG. 7 depicts a grinding burr mounted at a right angle with respect to the main shaft sleeve. This type of burr, in conjunction with stationary alignment clamp, can be used to prepare a smoothly curved surface on a femoral condyle.

Grinding tools also can be provided with an angled component, as shown in FIG. 7, so that a rotating angled burr 156 is mounted at an angle (such as a right angle) respective to the main shaft sleeve 158. This type of device can be provided by using a shaft assembly that includes (i) non-rotating outer sleeves, in two segments, (ii) rotating internal shafts, also in two segments, coupled to each other via conical gears or other suitable means. Alternately, this type of angled shaft assembly can use a chain-type mechanism which travels through the main shaft sleeve 158; the chain can drive a sprocket, which in turn will drive angled burr 156. As another alternative, a tool having the same net effect and operability can be provided by other means such as, for example using a tool with a gradual curve rather than a sharp angle, with a series of gimbal-type "universal joint" rotating components inside the outer sleeve.

Guides and Templates

Figure 8:
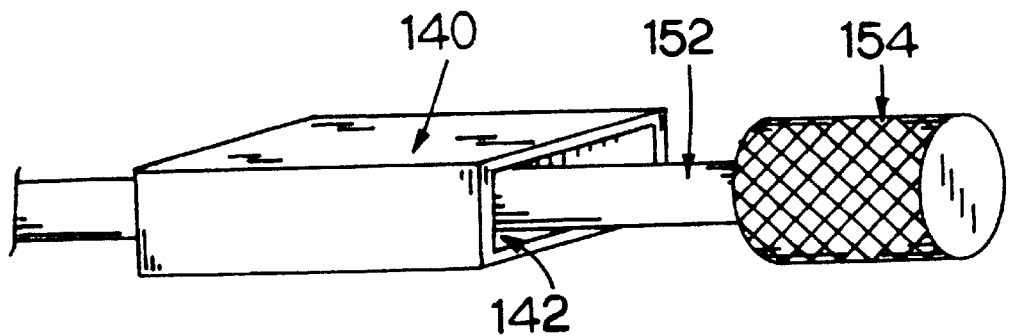
FIG. 8 depicts a slotted burr guide which holds and constrains the shaft of a rotating grinding tool, to help a surgeon create a precise and reproducible surface on a bone condyle that is being prepared to receive a scaffold implant.

In the embodiment shown in FIG. 8, the tool shaft sleeve 152 passes through slotted burr guide 140, which is temporarily mounted on top of the stabilizing platform 102. Slotted burr guide 140 has a slot 142 passing through it. This slot 142 holds and constrains the shaft sleeve 152.

In one type of slotted burr guide, which can be regarded as an alignment or template guide, the slot 142 in slotted burr guide 140 is only slightly larger (in its narrow dimension) than the diameter of non-rotating shaft sleeve 152.

The sizing of slot 142 prevents wobbling or other loose motion of the shaft in any undesired direction. The grinding burr 154 therefore can be moved back and forth across the length of slot 142, but the burr 154 cannot go beyond the reach of slot 142.

Figure 9:
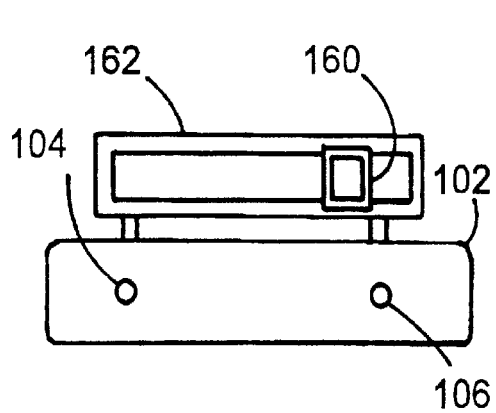
FIG. 9 shows a slotted burr guide with a movable square sleeve, to prevent any angling of a grinding or other tool which passes through the sleeve.

FIG. 9 shows a slotted burr guide with an even tighter constraint, comprising a square sleeve 160 that is part of the slotted guide assembly. This type of square sleeve 160, which can slide left or right inside slot 162, prevents any angling of a burr head in any direction, while allowing the burr head to be extended or retracted and moved solely to the left or right. This type of alignment guide can be used in preparing, for example, a flat and horizontal tibial plateau, on either side (or both sides) of the tibial spine (i.e., the small promontory in the center of the tibial plateau), as shown in FIG. 4.

Figure 10:
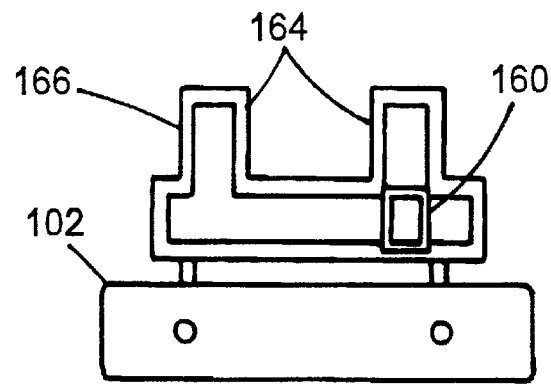
FIG. 10 shows a slotted burr guide that allows the burr head to be tilted upward, but only at two specific positions, to assist in preparing a flat tibial plateau that is provided with a groove at either or both of two fixed location, to accommodate a scaffold envelope with a "keel" structure as shown in FIG. 5.

FIG. 10 shows a slotted burr guide that allows the burr head to be tilted upward, but only at two specific vertical slots 164, positioned along the travel path of the slotted burr guide 166. This type of slotted burr guide 166 can assist in preparation of a flat tibial plateau that is provided with a groove at a fixed location (by angling the grinding tool downward at a vertical slot 164), to accommodate a scaffold envelope that has a "keel" structure as illustrated by the groove-and-keel arrangement shown in FIG. 15.

If desired, a slotted burr guide can also be provided with mechanical means (such as a detente inside slot 142, which interacts with a raised ring on rotating shaft 152) to limit and control the extension of the grinding burr 154 into the knee joint.

The types of slotted burr guides discussed above can be used, in conjunction with a device called a "goniometer", to create both (i) flat (i.e., single-planar) bone surfaces, such as for a tibial scaffold, and (ii) "faceted" bone surfaces, such as faceted femoral surfaces 99 as shown in FIG. 3. Faceted femoral surfaces are widely used in conventional "total knee replacement" operations, using open-knee surgery. A goniometer is a device that can precisely measure the angle of a knee, at any given position of flexion or extension. A goniometer can be used, in conjunction with one or more slotted burr guides, to create a set of vertical, horizontal, and angled (also called "chamfered") surfaces on a femoral condyle, as shown in FIG. 3. These facets can provide a solid and secure attachment for a femoral scaffold envelope having a faceted anchoring membrane.

In an alternate type of machining guide, a completely stationary clamp 140A (as shown in FIG. 7) can be affixed to the tibial stabilizer platform 102, to securely hold a shaft sleeve 162 in an absolutely fixed position while the patient's foot and calf are slowly lifted and lowered by the surgeon, to rotate the knee joint and tibia while the femur remains stationary and horizontal. This type of stationary clamp 140A can be used with a grinding burr 160 that rotates at a right angle with respect to the main shaft sleeve 162, as shown in FIG. 7, to prepare a femoral condyle surface. During this procedure, the patient will be lying flat on his back or sitting in a chair, with his thigh and femur bone horizontal. The calf of the patient's leg is moved up and down slowly, through various stages of flexion (i.e., where the knee is bent and the calf and tibia point downward) and extension (i.e., where the knee is straight and the calf and tibia are horizontal). As the calf and the tibia bone are slowly moved up and down, the rotating burr (which is securely affixed to the platform that is affixed to the front of the tibia bone) will be slowly moved across the surface of the femoral condyle, to grind away any cartilage and prepare the condyle to receive a scaffold implant. This will generate a smoothly rounded femoral condyle bone surface, which can accommodate the type of femoral scaffold envelope shown in FIG. 2.

If this approach to preparing the bone surface is used, it must be recognized that the femoral condyles are "cam" structures, i.e., they have a somewhat elliptical or cycloid shape with a varying radius, rather than being truly circular with a single radius. When the knee is fully extended and the leg is straight, the smallest portion of the cam structure articulates with the tibial plateau. As the knee is bent through progressively higher degrees of flexion, the distance between the center point of the femoral condyle and the outermost rim of the condyle grows larger, and the tibial plateau is pushed farther away from the center point of the femoral condyle, by the gradually increasing radius between the center point and the rim of the condyle. The cam differential varies between different individuals; in most adults, the cam differential is usually somewhere between about 4 mm and about 12 mm.

A rounded bone surface with the natural cammed structure can be generated using any of several approaches in the design of the stabilizing and aligning tools and guides. As one example, as shown in shown FIGS. 5 and 6, platform 102 can be coupled directly to the tibia bone 95 by means of fixed pins 104 and 106, and can also be coupled to the femur bone 90 by means of cam structures incorporated into femoral hinges 116. These femoral hinges 116 are positioned at the two ends 118 and 120 of a steel pin that has been positioned in a hole that has been drilled sideways through femur bone 90. Any suitable type of bracing or clamping system can be used to prevent the pin from rotating; for example, a strap-on brace can be fastened around the patient's thigh, and this brace can be used to clamp both ends of 118 and 120 of the femoral pin, which can be provided with a faceted or other non-round or non-smooth surface, to ensure that it cannot rotate once it has been clamped.

If cammed femoral hinges 116 are provided on both sides of the femur, the two struts 114 will be pushed downward (toward the patient's foot) a small distance as the calf and tibia are moved from an extended (horizontal) position into a flexed (downward) position. This cammed extension preferably should be the same distance as the femoral cam differential in the patient; that distance can be determined, before an operation begins, by measuring an X-ray or MRI image.

Figure 17:
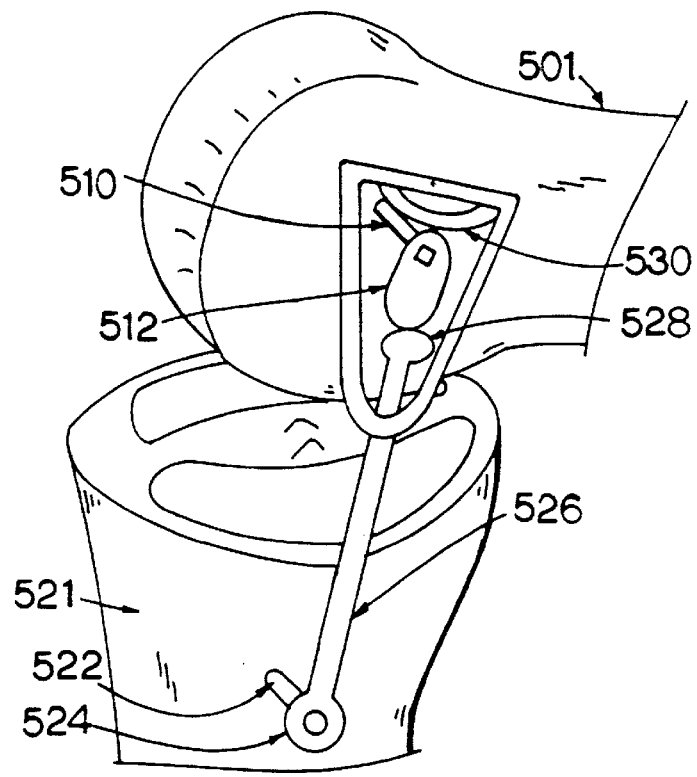
FIG. 17 depicts a bone alignment device which uses both a transverse femoral pin and a transverse tibial pin, with a cammed hinge at the femoral pin and a rigid strut positioned between the two pins, to ensure proper alignment of the femur and tibia at all stages of flexion and extension of the knee.

Cammed femoral hinges 116 can incorporate any of several suitable mechanisms that will provide the desired result. In one such mechanism, shown in FIG. 17, the head of each hinge can comprise an actual cam disk, mounted in a plane that is perpendicular to the shafts provided by pins 118 and 120. Each of the two struts 114 can be provided with an anvil-type upper end, which will press and ride against the cam disk as the knee is flexed or extended. To eliminate any undesired motion, the anvils at the end of struts 114 can be held tightly against the cam disk, during rotation, by means such as a spring-loaded constraining device on the struts 114. The drawing of this structure in FIG. 17 is a simplistic depiction, intended solely to convey a visual impression that the femoral pin terminates in a cammed device; in actual practice, a different cammed structure would likely be used. Various such devices are known for generating a cammed path of motion, such as devices which include (i) protruding pins that travel within slotted structures having the desired shapes, and (ii) rotating disks that are mounted in an eccentric (off-center) manner on an axle.

It should be noted that struts 114, as shown in FIG. 6, are angled somewhat, since the hinges 112, which flank the tibial stabilizing platform 102, are not in a direct line with the center of the tibial bone, and are offset from it in the anterior direction. If desired, any of several approaches can be used to accommodate for that fact while still providing anatomically precise alignment of the femoral condyles and tibial plateaus during a grinding procedure or other alteration. In one method, the size and shape of the camming structure in the femoral hinges 116 can be adjusted somewhat, to account and adjust for the offset distance (i.e., in FIG. 6, the horizontal distance between the actual tibial hinges 112, and an imaginary centerline drawn through the center of the tibial bone at that same height).

As a second option, tibial platform 102 can be fitted with lateral extensions on both sides. These extensions can curve or otherwise extend partway around the calf and tibia, to a point where they can position the tibial hinges 112 in exact desired locations, on both sides of the tibial bone and squarely flanking it with no offsetting factor. If this second option is chosen, the tibial platform can be reinforced, to prevent or minimize any bending or torsional forces, by means of a clamping device that can be strapped around the calf.

As a third option, which is illustrated in FIG. 17, pin 510 is driven transversely through femur bone 501, and is provided with a cam device (such as cam-shaped disk 512, coupled to the end of pin 510). An additional hole is also drilled transversely through the center of the tibia bone 521, and a tibial pin 522 is driven through the tibial hole. A hinge or other coupling 524 is mounted at each end of the tibial pin 522. This coupling connects to a rigid strut 526, which has an anvil component 528 at its other end, which presses against the femoral cam disk 512, held against it by spring-loaded device 530.

Routine tests on animals or human cadavers can determine whether a simple adjustment to the size or mechanism of the cammed femoral hinges 116 will allow that approach to be used, since it may provide the simplest and easiest solution to any problems that might be caused by the tibial offset factor. Similar tests can also evaluate any other candidate approach to providing the cammed action discussed herein.

Using the various components and methods discussed above, various types of alignment guides can be used to carefully constrain the path and reach of a grinding or polishing tool inside a knee joint, while keeping the tibia and femur bones properly and precisely aligned. By moving the tool back and forth inside slot 142, a high-speed rotating burr is carried through a grinding or polishing path that generates a desired shape (flat, faceted, or curved) on a femoral condyle or tibial plateau, to ensure a close fit between the prepared bone surface and the scaffold implant that will be anchored to that bone surface.

In other types of slotted burr guides, a slot can allow a wider degree of motion by the shaft and the burr. This type of slotted guide can be used by a surgeon as a stabilizer, rather than a template, to give the surgeon a steady base for better leverage and control over the shaft 152 of the grinding tool 150. In a manner comparable to a photographer resting one elbow on a solid surface while holding a camera, this can help the surgeon exert better control over the grinding or polishing actions of the tool.

Figure 11:
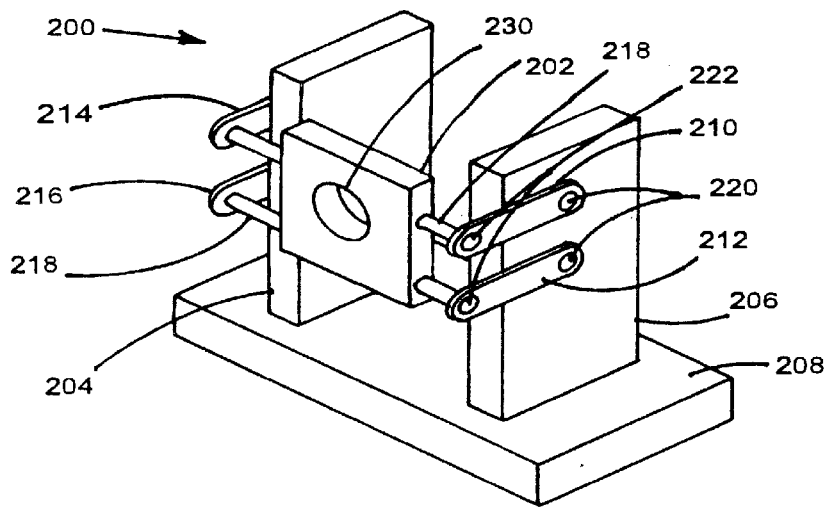
FIG. 11 depicts a "travelling guide" which moves in a constrained path while tightly holding a grinding tool. By varying the lengths and fixation points of the rotatable struts which hold the travelling guide, this type of guide can be constrained to either a perfectly circular path, or an elliptical, cycloidal, or other cam-like path.

Various other types of mechanical devices (including devices referred to herein as "travelling guides", which move in a fixed and constrained path while tightly holding a tool) can also be used to guide and properly constrain the motion of a grinding or polishing tool. As one example, assembly 200, shown in FIG. 11, comprises a travelling guide 202 mounted between two fixed vertical supports 204 and 206, both of which are permanently mounted on a working platform 208, which can be detachably mounted on the tibial stabilizing platform 102 shown in FIGS. 5 through 7.

Travelling guide 202 is coupled to the fixed vertical supports 204 and 206 via a total of four rotating struts 210–216, with two struts coupled to each side of guide 202 via a lateral pin 218. Each strut 210–216 can rotate about a first fixed pin or hinge 220 which is mounted on a fixed vertical support 204 or 206. In addition, the movable end of each strut is coupled to a second rotatable pin or hinge 222. This arrangement, as shown, allows all four struts to move together in a linked manner, coupled to the centered guide 202 which can travel upwards or downwards in an arc.

Travelling guide 202 is shown in a simplified manner, with orifice 230 passing through it to hold a burr shaft or other tool. In actual use, orifice 230 should be provided with a clamp or other securing device so that a burr tool can be placed in the guide and locked in securely, to avoid unwanted wobble, extension, or other motion during use.

This type of travelling guide can be used to establish a reproducible arc which is aligned in a way that can be used to prepare a femoral condyle for implantation of a scaffold envelope. If the lengths of all four struts are identical, and if the vertical spacing between the travelling pins 222 is identical to the vertical spacing of the fixed pins 220, travelling guide 202 will pass through a simple circular arc, having a radius equal to the lengths of the struts. By contrast, if the top struts 210 and 214 have a different length from the bottom struts 212 and 216, or if the vertical spacing between the travelling pins 222 is different from the vertical spacing between the fixed pins 220, then travelling guide 202 (and any grinding burr or other tool that is secured in the guide 202) can be given any of a variety of curved or elliptiform, yet constant and reproducible, pathways. Accordingly, this type of travelling guide can be used, to enable a surgeon to quickly and reliably generate uniform and predictable curved surfaces for mounting scaffold envelopes on prepared bone surfaces.

If desired, a similar approach can be used to grind precise and consistent rounded or elliptiform shapes in tibial plateaus, by altering the size and shape of the vertical supports 204 and 206 (if necessary) and by altering the placement of the fixed pins 220 so that they have a more horizontal alignment.

Figure 12:
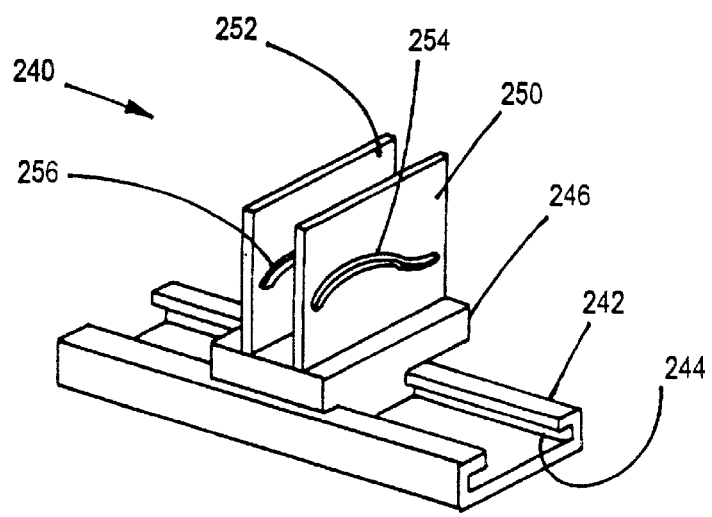
FIG. 12 depicts a penetration guide with vertical supports having two curved slots, which will constrain and guide the motion of a tool with protruding lateral pins on both sides of the shaft sleeve.

Any number of other types of alignment guide and/or templates can be used, if desired. As one example, a penetration guide 240 shown in FIG. 12 has a fixed horizontal base 242 with a track structure 244 that holds a slidable base 246, which can be securely clamped at any fixed location along the lateral span of fixed base 242, to establish a working position. Slidable base 246 supports two fixed vertical supports 250 and 252, which are parallel to each other, similar to the supports 204 and 206 in FIG. 11 but closer to each other. Vertical supports 250 and 252 have matching parallel curved slots 254 and 256, as shown in FIG. 12. These matching slots 254 and 256 can have any desired shape and size, include any desired type of curve. A tool shaft (not shown) with a grinding burr at its tip is provided with two fixed lateral pins extending outwardly from each side of the shaft sleeve. These lateral pins will engage slots 254 and 256 in the vertical supports 250 and 252. The lateral pins on the tool shaft will be constrained within the parallel slots 254 and 256, and will be able to move back and forth only within those slots. Accordingly, the shape and curvature of the two slots 254 and 256 will control the pathway of a grinding burr or similar tool mounted at the tip of the tool shaft.

This type of penetration guide allows a surgeon to carefully and reproducibly control the path and travel of a grinding burr or other tool as it extends and penetrates farther and deeper into a joint being repaired. By contrast, the slotted guides shown in FIGS. 6 through 10 will mainly control lateral motion of a tool.

Various other types of fixed or travelling guides, templates, and other aids that are useful and helpful for rapidly and reliably machining and shaping a hard surface into an exact desired shape are well known to machinists and mechanical engineers, and are used in various types of machines, machine shops, carpentry and furniture shops, etc. Such devices include mechanisms that are linked, by gears or other devices, in a manner which provides three-dimensional control over the path of a rotating burr.

Alternately or additionally, computerized control systems can also be used, in which a computer is programmed to operate a device that moves a rotating burr, laser, or other tool through a complex two- or three-dimensional pathway. This can be done, using hardware and software interactions that are comparable to what happens when a graphic plotter moves a pen or inkjet through a highly complex pathway while printing a map, blueprint, or other complex drawing. The hardware and software used in such computerized control systems are well known to people skilled in the art of designing and manufacturing computer-controlled machining systems and other computer-controlled mechanical devices.

Accordingly, the suitability of any known mechanical, electrical, or computerized control system, to help facilitate surgical and/or arthroscopic preparation of a bone surface so it can receive a scaffold envelope as disclosed herein, can be evaluated by those skilled in the art, using no more than routine experimentation.

It should also be noted that a variety of different tool guides can be interchangeably mounted on tibial platform 102 during various different stages of the arthroscopic procedure. For example, a "femoral prep" set of devices can be used to help prepare a femoral condyle, and a "tibial prep" set of device can be used to prepare a tibial plateau. Subsequently, after the scaffold envelopes have been inserted, anchored to the bones, filled to the proper level with a hard-setting compound, and allowed to set into hardened configurations, "femoral finish" guides and tools can help the surgeon finish and fine-tune the femoral implant, and "tibial finish" guides and tools can help the surgeon finish and fine-tune the tibial implant.

Various other types of devices also can be used, in conjunction with a fixed stabilizing platform and interchangeable guides or templates, to complement and support any desired step in the arthroscopic procedure. For example, depending on the type of polymer or other material used to create an implanted scaffold, a curved spatula with an electric heating element, which renders the surface of the spatula hot enough to melt a thin outer layer of the implant scaffold, may be used to momentarily liquify the polished surface of an implanted scaffold, so that the melted surface layer, upon cooling, will harden into a surface that is smoother than can be obtained by abrasive polishing. Alternately or additionally, laser devices, razor-sharp slowly rotating blades which can cut cleanly through the solidified polymer, and other such tools can be used, rather than abrasive grinding tools, during the final fine-tuning stages of an operation.

In addition to removing the entire layer of native cartilage in the region that is to replaced by a synthetic implant, a surgeon can also remove a significant amount of the outermost bone surface. For example, in preparing a femoral condyle or tibial plateau, a surgeon can sculpt a "bed" in the bone, ranging from about 1 to 3 mm deep (about $\frac{1}{16}$ to $\frac{1}{8}$ inch) around the periphery of the bed, increasing to a maximum of about 6 to 10 mm deep in the center of the bed. This approach can help accomplish several goals. First, it can help provide a relatively flat and gradually-curved surface for anchoring the scaffold, instead of forcing the scaffold to adapt itself to each and every small variation or curvature in a bone surface. Second, it can help ensure that the scaffold is anchored solidly and securely to fully-hardened bone, rather than to an interface region where the bone tissue makes a transition to cartilage tissue. Third, it can allow the scaffold to be made thicker, which means it can be stronger and more durable than a thin layer, and it can provide better cushioning and shock absorption than a thin layer coated on top of a hard surface. Fourth, it allows blunt edges to be provided around the periphery of the scaffold envelope, to avoid the need for fully angular tapers with paper-thin peripheral edges, which might become detached, frayed, or otherwise damaged. And fifth, it makes the anchoring process easier and more reliable, and avoids or minimizes any protrusions or surface irregularities that might jeopardize the success and durability of the cartilage replacement.

Implanting, Cementing, Anchoring, and Filling a Scaffold

As noted above, two of the characteristics of a scaffold envelope suitable for use as described herein include: (i) it must be suited for insertion into a joint through a minimally-invasive incision, as commonly used in arthroscopic surgery, while the envelope is empty; and, (ii) after it has been inserted and properly anchored to a bone surface, it must be filled with a fluidized compound that will set and harden into a desired final shape, so that the resulting hardened structure can effectively replace a segment of diseased or damaged cartilage that has been removed by the surgeon.

In order to promote these goals, a scaffold intended for use as disclosed herein preferably should be manufactured in a way that causes it to seek and settle into a certain desirable shape. For example, an implant for a femoral condyle will have a certain shape and size, with a relatively pronounced curvature; by contrast, an implant for a tibial plateau will have a significantly lesser degree of curvature, and in one preferred embodiment will have an essentially flat anchoring surface.

Such scaffolds can be created by fabricating the scaffold envelope from a flexible material that has a "three-dimensional memory". This means that after it has been molded and set in a certain desired shape, it can be twisted, squeezed, or otherwise manipulated to allow insertion of the empty scaffold into a joint through a relatively small skin incision, with the aid of an insertion tube if desired. Subsequently, after the pressure, tension, or other force has been released from the scaffold, the rubbery elastic material will seek to return to its original molded shape.

Additionally, if desired, a scaffold envelope can contain one or more internal reinforcing structures. These can be similar to the internal straps and other devices used in inflatable air mattresses, to cause such air mattresses to inflate into relatively flat (rather than spherical) shapes. For example, if a femoral condyle scaffold is provided with several internal reinforcing straps, evenly distributed across the area of the envelope, those straps would provide substantial assistance in helping the envelope generate a desired, relatively uniform thickness as it is inflated with a fluidized compound.

Alternately or additionally, a scaffold envelope can be provided with one or more internal reinforcing "runners" or "vanes" that extend parallel to the longest dimension of the envelope. As noted above, if this type of internal runner is used, it can also serve as a baffle, to provide a single flow path from the inlet orifice to the outlet orifice. In this design, polymeric fluid which is being injected into the scaffold will progressively force any gas or liquid in the collapsed matrix toward the outlet tube, as the envelope fills up with the injected polymer.

As yet another approach, a multi-chambered device can be provided, wherein each chamber tries to seek a certain size and shape as it is filled with the fluidized polymer.

Once a scaffold has been inserted into a joint, it is released from any squeezing or other constraint or force that was used to insert it through the skin incision. In some cases (for example, if a flexible scaffold was packaged and sealed under vacuum conditions), it may be easier to work with and manipulate the scaffold inside the joint if it is partially filled with the liquid polymeric compound, so it can assume a near-normal size and posture with no internal vacuum or other distorting forces on it, but without expanding to its completely-filled size.

Once the scaffold has been properly positioned over the prepared bone surface, to make sure they align properly and that both contacting surfaces are ready to be cemented together, a layer of a suitable cement that adheres tightly and permanently to both surfaces (such as a polymethylmethacrylate) is applied to either or both surfaces. The surfaces are then pressed together firmly, the scaffold is gently but firmly pressed and tamped down by the surgeon using an appropriate tool, and any anchor pins, staples, or other such devices are driven through any anchoring flaps or other accommodating components. The cement and anchors, working together, will permanently affix the anchoring membrane of the scaffold to the prepared bone surface.

After the cementing and anchoring steps have been completed, and after the cement has been given some time to at least partially set, the scaffold is then filled with the remaining desired quantity of polymeric liquid, to expand and enlarge the scaffold to its final desired thickness. While the injected polymer is setting and gradually hardening, the outer articulating surface of the scaffold can be manipulated and shaped in various ways, so it will have the desired final shape and contours after the polymer inside the scaffold fully sets and hardens.

Figure 13:
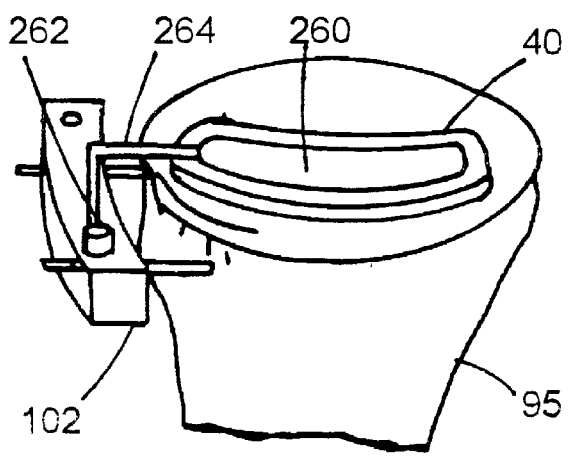
FIG. 13 depicts a surface-shaping guide that is inserted into a knee joint and held in position adjacent to a tibial scaffold while the scaffold is being filled.

To minimize the need for final polishing of a fully set and hardened implant, a surgeon can use various shaping and manipulating devices (both active and passive, such as spatulas, depressors, templates, shaping guides, etc.) to help ensure that an implanted scaffold is molded, pressed, or otherwise shaped or sculpted into a desired shape after the setting compound has been injected into the scaffold, but before it fully sets and hardens. For example, FIG. 13 illustrates placement of a passive surface guide 260, which can be inserted arthroscopically into a knee joint. During the polymeric filling operation, guide 260 is held in position by a mounting attachment 262, which is affixed to the tibial platform 102, and a positioning arm 264. This type of passive guide does not need to be large and wide; instead, its main purpose is to ensure that the center of the tibial scaffold 40 rises to the desired height, and no further, as it is being filled.

After the injectable compound has set into a final shape, the surgeon can use the various sculpting and cutting tools to finish and "fine-tune" the surface of the hardened scaffold into the desired final shape, as discussed above. The inlet tube (and outlet tube, if present) can be cut off from the scaffold envelope, using an arthroscopic scalpel or scissors inside the knee joint. This cut preferably should be flush with the surface of the envelope, so that a remnant of the tube does not protrude outwardly; however, so long as the tube inlet has been positioned properly, away from any articulating or load-bearing surface, a small blunt stump should not cause substantial problems. The remainder of the tube is pulled out of the knee joint, any additional work that may be necessary is completed by the surgeon. The skin incisions are closed and sutured, stapled, or otherwise secured, to complete the surgery.

Polymeric Materials

Scaffold envelopes as disclosed herein can be made from any selected polymeric or other suitable material that has a suitable combination of flexibility, biocompatability (which includes traits such as low levels of thrombogenicity), strength, and resistance to wear and abrasion. A great deal of work has been done on biocompatible polymers, as reviewed in various publications such as Peppas et al 1994, Silver 1994, Hubbell 1995, Stokes 1995, Burg et al 1997, Lewis 1997, Kim and Mooney 1998, and Ambrosio et al 1998. Accordingly, various types of polymers having the desired combination of traits are known to those skilled in the art.

It also should be recognized that the final "stiffness" of most non-rigid polymers can be controlled, to achieve nearly any desired level of non-rigid stiffness, by controlling various factors such as (i) crosslinking conditions, (ii) the type and concentration of any crosslinking agents that are mixed with a monomeric or pre-polymeric building block, and (iii) the type and quantity of other chemical agents that will truncate, quench, or otherwise modify a crosslinking reaction.

In general, the net result of controlling these factors (and other factors that are known to chemists and others who develop and design biocompatible polymers) is to control any or all of the following: (i) the average molecular weight of a resulting polymer; (ii) the density and chemical structure of the crosslinking bonds which couple long polymeric backbones to each other; and (iii) the length, density, and other traits of side chains that become wrapped around and entangled with each other, in the complicated molecular meshworks that generate most types of strong and resilient but non-rigid polymers.

Since scaffolding envelopes can be manufactured under completely non-physiological conditions, in a "clean room" type of factory or laboratory, a fairly wide variety of elastomeric polymer classes offer good candidates for evaluation for such use. Two particular types of elastomeric polymers that are likely to be well-suited for such use include polycarbonate polyurethanes, described in articles such as Stokes et al 1995, and perfluorinated elastomers, described in items such as U.S. Pat. Nos. 4,621,107 and 4,900,793 (Lagow et al, 1986 and 1990).

A polymeric or pre-polymeric compound or mixture that is to be injected into a scaffold envelope preferably should set and harden at body temperatures, without requiring ultraviolet radiation, high temperatures, or other non-physiologic conditions. Such polymers are sometimes referred to as "cold-setting" polymers, since they do not require high temperatures. Since most crosslinking reactions are exothermic (i.e., they release energy), a cold-setting polymer may reach a somewhat elevated temperature, comparable to hot bathwater; however, such reactions generally should not create temperatures that reach or approach the melting temperature of a polymer.

In general, most types of "cold-setting" polymers that do not require prolonged curing times contain at least three chemical components: (i) at least one type of monomeric or other relatively small building block; (ii) at least one type of chemical crosslinking agent, which normally must be kept separate from the monomer until they are ready to be mixed together and injected as a mixture; (iii) optionally, an additional reagent to help ensure that the resulting polymer has a desired average chain length and desired levels of crosslinking and side-chains, to help ensure that the final polymer has the desired characteristics after it sets and hardens.

Various polymeric mixtures that are mixed immediately before use (in a manner comparable to epoxy) can set and harden within less than an hour. By contrast, pre-mixed compounds (such as the silicon rubber compounds typically sold in tubes that fit into caulking guns) usually require substantially longer to set and harden, so that a solvent which keeps the compound in liquified form inside the tube can permeate out of the compound as it sets, once it is exposed to air. Since rapid setting times are very important whenever a patient is being kept anesthetized, polymeric compounds that require only about 5 to 15 minutes to set and harden are preferred over compounds that require more than an hour.

The filling polymer does not need to have very high levels of biocompatability, since it normally will remain completely sealed inside a scaffold envelope, and will not come into direct contact with tissues or body fluids. However, since there will always be some risk of damage to the knee (such as in an accident) that might somehow rupture the scaffold envelope, any polymer that is used in a surgical implant preferably should be biocompatible, in case any unplanned contact occurs between the polymer and any body fluids or tissues.

The filling polymer does not need to be made of the same material as the scaffold, so long as the filling polymer can form a strong and durable bond with a pre-formed surface inside the scaffold. If desired, the envelope and the filler polymer can be different types of polymers or other materials which have substantially different physical characteristics. For example, if desired, the scaffold envelope can be made out of a relatively soft and rubbery material, while the filler polymer is harder and closer to rigid; this would allow maximum flexibility and manipulation of a highly flexible unfilled scaffold envelope, during arthroscopic insertion and implantation. Alternately, a scaffold can be made of a relatively stiff material, for greater durability and resistance to wear and abrasion, while the filler material can be a softer and more elastic material, or a semi-liquid gel or polymer-gel mixture.

As another alternative, the articulating surface of a scaffold envelope can have a metallic external layer, which can function as both (i) a mechanical spring device, to help ensure that the envelope seeks and obtains its desired final shape after it has been inserted into the knee; and (ii) a smooth and durable surface that is highly resistant to abrasion and wear. Such metal-coated scaffold envelopes can be modelled after the metal-on-plastic "total knee replacement" implants that are used under the prior art, using open-knee surgery.

Patellar Implants; Preparation and Scaffolding Options

As noted above, scaffold envelopes as disclosed herein also can be used to replace damaged cartilage segments on either or both of the articulating surfaces between the patella (the kneecap) and the femur. Because it is easier to illustrate the relatively simple patello-femoral compartment than the more complex femoral-tibial compartments, the discussion in this section is also used to describe and illustrate various options and enhancements that can be used with implants for femoral condyles or tibial plateaus, if desired.

Figure 14:
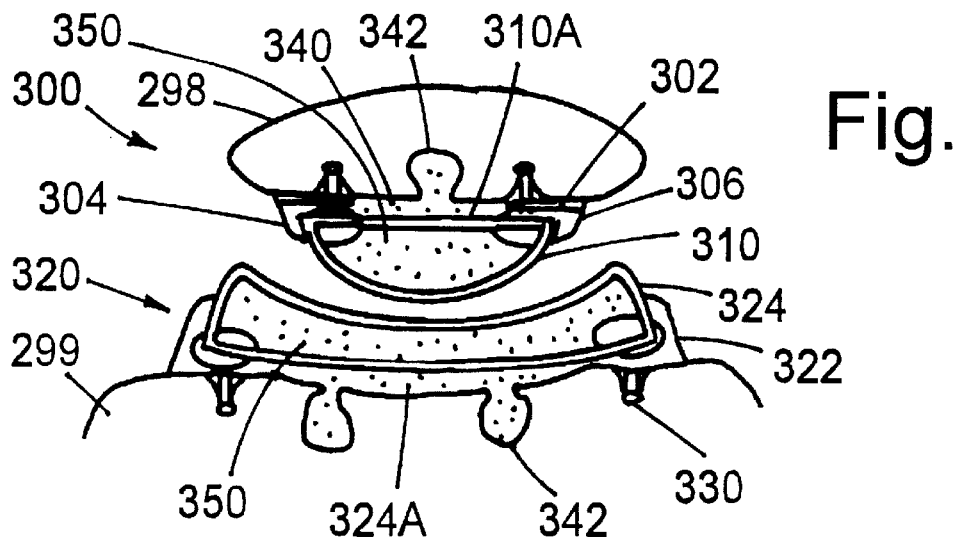
FIG. 14 is a cross-section of a patello-femoral joint, which illustrates, on both bone surfaces: (i) an implanted positioning ring which is anchored to a bone surface and which has an open center; and (ii) a scaffold envelope which is secured inside the positioning ring.

FIG. 14 illustrates the use of two distinct implants on the patellar bone 298, as well as two distinct implants on anterior femoral surface 299. Patellar implant 300 comprises a positioning ring 302 (shown in cross-section as angled rim cross-sections 304 and 306), and a patellar scaffold envelope 310. Similarly, femoral implant 320 comprises a positioning ring 322 and a femoral envelope 324.

Positioning rings 302 and 322 are each made of a single rim-shaped piece of material, with tabs, lugs, or other extensions or components that can be secured to the bone by anchor devices 330, spaced at suitable locations around the rim (either inside the ring, outside the ring, or both).

A positioning ring 302 or 322 does not have an envelope structure, and is not inflatable. In a preferred embodiment, it has an open center with no membrane covering the middle, so that it can be easily manipulated and positioned by a surgeon during a positioning and anchoring procedure.

For each implant 300 or 320, after the bone surface has been prepared and the damaged segment of cartilage has been fully removed by a grinding operation as described above, the positioning ring 302 (or 322) is inserted into the joint, and carefully placed and positioned on the prepared bone surface. After the anchors 330 have been set into the bone, with the assistance of cement if desired, the ring is complete and ready to receive a scaffold envelope.

A scaffold envelope 310 (or 324) is then inserted through a skin incision into the knee joint in folded or rolled form. After insertion, it is unfolded or unrolled into a relatively flat unfilled shape. A suitable quantity of cement 340 is injected between it and the prepared bone surface, and the cement is spread evenly across the contact surface, using a device such as a spatula tip. To help stabilize and strengthen the cemented attachment, one or more grooves or holes 342 can be drilled, grinded, or otherwise created in the bone surface, as shown by cement holes 342; if such indentations were created, they are carefully filled with cement. The anchoring membrane 310A (or 324A) of the scaffold envelope 310 (or 324) is then pressed against the wet cement that covers the bone surface, inside the positioning ring 302 (or 322).

After the cementing operation, envelope 310 (or 324) is filled with polymeric compound 350, causing the envelope to expand to a desired final shape. If desired, the scaffold envelope 310 or 324 can also be provided with anchoring tabs; alternately, if animal and clinical tests indicate that pin-type anchoring of the envelope is not necessary, and gluing is sufficient in combination with a positioning ring (this may be valid either for certain types of patients, such as elderly patients who will not subject the joint to severe stresses, or possibly for all patients), it may be possible to eliminate anchoring of an envelope 310 or 324. In such cases, permanent securing of the envelope would rely on cementing in conjunction with the positioning ring.

FIG. 15 shows a similar set of patello-femoral implants, illustrating two significant differences. Patellar scaffold envelope 370 is coated with a metallic layer 372. This dome-shaped layer is thin enough to allow it to be flexed and bent into a somewhat flattened semi-circle configuration, to allow it to be inserted into a knee joint through a minimally invasive incision.

In addition, femoral implant 380 is provided with a "keel" 382 on its anchoring surface. Keel 382 extends into a groove or hole 384, which has been grinded or drilled into the anterior surface of femoral bone 299. This arrangement increases the stability and strength of the anchoring for the implant. As mentioned above, this type of approach can also be used to increase the stability and strength of other types of implants as well, including implants on femoral condyles or tibial plateaus.

It should also be noted that the positioning rings discussed above may also be useful in at least two other ways; accordingly, they are claimed herein in their own right.

First, a positioning ring can be marked, with a plurality of visible markings, to help them serve as location guides during an arthroscopic procedure. The difficulties and complexities of working arthroscopically inside a knee are considerable, in view of the complex obstacles posed by the numerous tendons, ligaments, and other forms of soft tissue in and around the knee joint. Accordingly, a convenient positioning guide in the shape of a ring with calibrated marks on it, if properly positioned in the area that is being worked on, would in quite a few cases be a very useful aid to the surgeon.

Second, positioning rings can also enable another type of surgical correction, involving so-called "salvage operations", most commonly used in frail and elderly patients whose ligaments and connective tissues around the knee joint are fragile and tenuous. In patients who have already suffered severe deterioration around the knee, any surgical intrusions that disrupt any of the remaining tissues in or around the knee, more extensively than is absolutely necessary, can seriously decrease the likelihood of a satisfactory recovery. Accordingly, in some patients that fall into this category, it may be preferable to simply inject a cold-setting polymer into a horizontal basin, formed by an anchored positioning ring as disclosed above. This approach would dispense with the sealed scaffold envelope, and instead would use the positioning ring to establish an open scaffold, comparable to the wooden or steel forms (also called scaffolds) that are used to shape concrete when it is poured.

Other Joints

Figure 16:
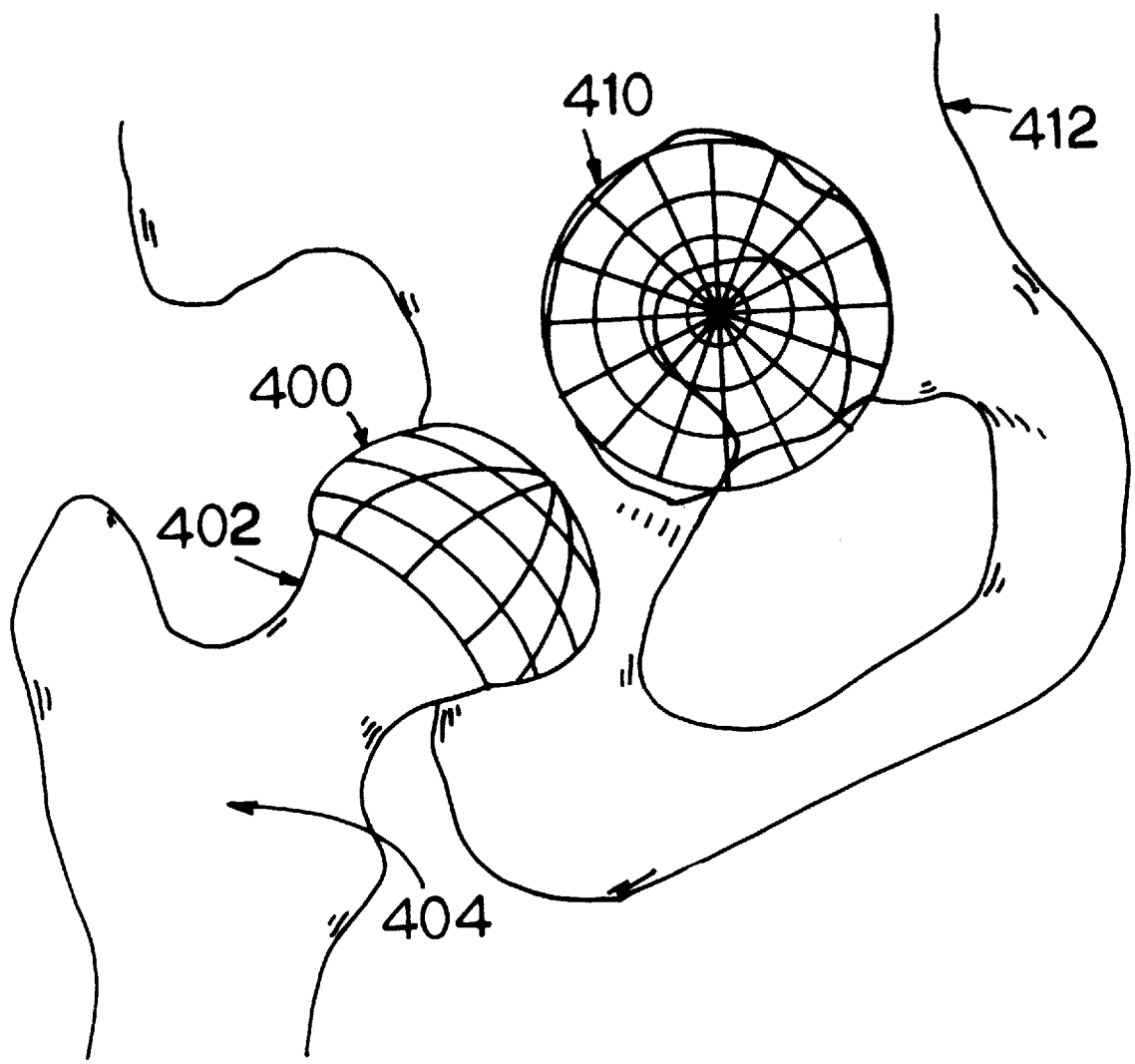
FIG. 16 depicts repair of a hip joint, using flexible scaffold envelopes that have been anchored to the articulating ball surface on the femur and socket surface in the pelvis.

As indicated in FIG. 16, flexible and inflatable scaffold envelopes in the shape of a rounded cup can be used to replace cartilage in ball-type joints, such as in the shoulder (the gleno-humeral joint) or hip (pelvic-femur joint). FIG. 16 depicts a first scaffold envelope 400, secured to the condyle ball 402 on femur bone 404, as well as a second scaffold envelope 410, secured to the socket surface of pelvic bone 412. Such scaffold envelopes can be used to replace either or both of the cartilage surfaces in a ball joint, using essentially the same methods as described herein.

Packaged Article of Manufacture

Figure 18:
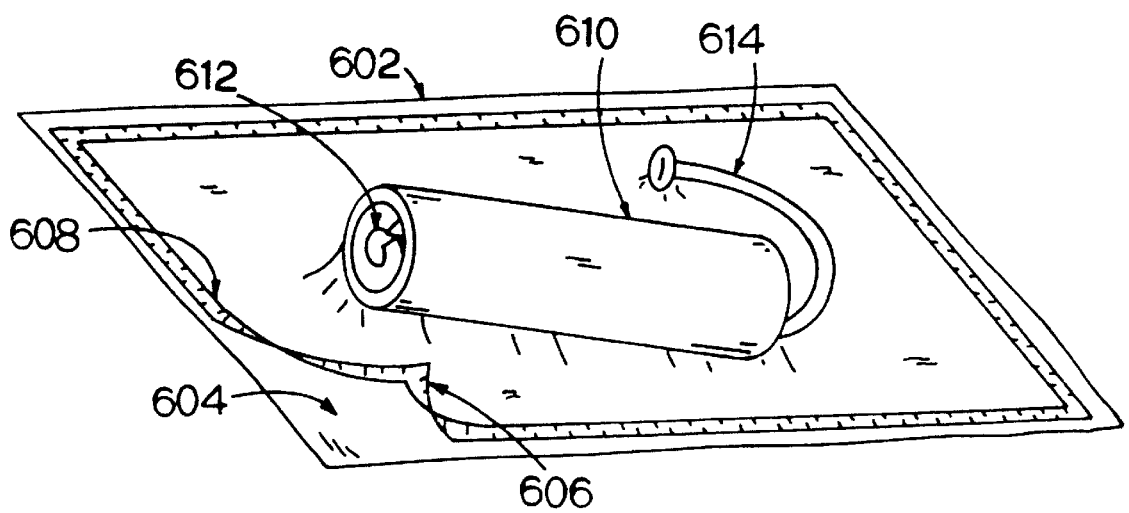
FIG. 18 depicts a flexible scaffold which has been rolled up and stuffed inside an arthroscopic insertion tube. The scaffold and insertion tube are both packaged inside a sealed plastic envelope which maintains sterility until ready for use.

Certain claims refer to an article of manufacture, comprising a sealed package containing a sterile flexible device as disclosed herein. An illustration of such a package is provided in FIG. 18. In this depiction, a vacuum-sealed plastic package 602 comprises bottom layer 604 and top layer 606, sealed to each other by a heat-sealed peripheral seal 608 (one corner of the top layer is shown lifted, solely for illustrative purposes). Enclosed within this sealed plastic package is an arthroscopic insertion tube 610, which contains a rolled-up scaffold envelope 612 inside the tube. A fluid inlet tube 614 extends out of one end of tube 610. This type of tube can be used to help a surgeon insert a tightly-compressed rubbery device through a small skin incision. Once the advancing tip of the tube has approached its intended location, the rolled-up scaffold is pushed out of the tube, with the aid of a blunt rod, plunger, or other suitable device. The surgeon then carefully works the scaffold into position, ensuring that it does not tear the skin incision or other vulnerable tissue as it returns to its molded shape.

Thus, there has been shown and described a new and useful means for using inflatable scaffold envelopes to replace segments of damaged cartilage in mammalian joints. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Ambrosio, L., et al, "Composite hydrogels for implants," *Proc Inst Mech Eng [H]* 212: 93–9 (1998)

Burg, K. J., et al, "Modulation of surface and bulk properties of biomedical polymers," *Annals N Y Acad Sci* 831: 217–22 (1997)

Brittberg, M., et al, "Treatment of deep cartilage defects in the knee with autologous chondrocyte transplantation," *New England J Medicine* 331: 889–895 (1994)

Chen, F. S., et al, "Chondrocyte transplantation and experimental treatment options for articular cartilage defects," *Amer J Orthopedics* 26: 396–406 (1997)

Hubbell, J. A., "Biomaterials in tissue engineering," *Biotechnology* 13: 565–76 (1995)

Kim, B. S. and Mooney, D. J., "Development of biocompatible synthetic extracellular matrices for tissue engineering," *Trends Biotechnol* 16: 224–30 (1998)

Lewis, G., "Polyethylene wear in total hip and knee arthroplasties," *J Biomed Mater Res* 38: 55–75 (1997)

Minas, T., et al, "Current concepts in the treatment of articular cartilage defects," *Orthopedics* 20: 525–538 (1997)

Silver, F. H., ed., *Biomaterials, Medical Devices and Tissue Engineering* (Chapman & Hall, 1994)

Stokes, K., et al, "Polyurethane elastomer biostability," *J Biomater Appl* 9: 321–54 (1995)

Thornhill, T. S., "Cartilage resurfacing: Facts, fictions, and facets," *Orthopedics* 20: 819–820 (1997)

What is claimed is:

1. A surgically implantable device for replacing a segment of damaged cartilage in a mammalian joint, comprising a flexible envelope suitable for surgical implantation in a joint, wherein the flexible envelope:

(i) is designed to be flexed into a shape that allows it to be surgically inserted into a joint having damaged cartilage, using arthroscopic tools and methods;

(ii) can be restored to a desired size and shape which is useful for replacing a segment of damaged cartilage, after the flexible envelope has been inserted into the joint through a skin incision;

(iii) is designed to be permanently anchored to a bone surface;

(iv) has a fluid inlet orifice which allows the flexible envelope to be filled, after it has been surgically inserted into a joint, with a fluidized compound that will set into a solidified material inside the flexible envelope, thereby creating a filled implant consisting essentially of an envelope and the material contained within the envelope, wherein the flexible envelope is suited in all respects for use in such manner, and thereby enables a surgeon to create inside a joint, using arthroscopic methods, a filled implant which is permanently anchored to a bone surface and is medically effective in replacing a damaged segment of cartilage.

2. The surgically implantable device of claim 1, which is made of a flexible synthetic polymer that is biocompatible, non-immunogenic, and not degraded or resorbed by bodily fluids.

3. The surgically implantable device of claim 1, which has an internal surface capable of forming a strong permanent bond with a cold-setting polymeric mixture used for insertion into the flexible envelope during an arthroscopic procedure.

4. The surgically implantable device of claim 1, which has a shape and size designed to replace a cartilage segment in a knee joint selected from the group consisting of a medial femoral condyle and a lateral femoral condyle.

5. The surgically implantable device of claim 1, which has a shape and size designed to replace an entire femoral cartilage surface which includes a medial femoral condyle, a lateral femoral condyle, and a femoral portion of a patello-femoral compartment.

6. The surgically implantable device of claim 1, which has a shape and size designed to replace a cartilage segment in a knee joint selected from the group consisting of a medial tibial plateau and a lateral tibial plateau.

7. The surgically implantable device of claim 1, which has a shape and size designed to replace a cartilage segment in a knee joint which includes both a medial tibial plateau and a lateral tibial plateau.

8. The surgically implantable device of claim 1, which has a shape and size designed to replace a patello-femoral cartilage segment in a knee joint.

9. The surgically implantable device of claim 1, which has a shape and size designed to replace a cartilage segment in a ball-and-socket joint.

10. The surgically implantable device of claim 1, which has a shape and size to replace a portion of an articulating cartilage segment in a mammalian joint.

11. A method of surgically replacing a segment of damaged cartilage in a mammalian joint, comprising the following steps:

(a) preparing a cartilage-bearing surface of a bone in a joint that has suffered damage to the cartilage, so that said surface is ready to receive a surgical implant that can replace the damaged cartilage;

(b) inserting into the joint a deformable envelope;

(c) positioning the deformable envelope over the surface of the bone which has been prepared as provided in step (a);

(d) permanently anchoring the deformable envelope to the surface of the bone, and filling the deformable envelope with a fluidized compound that will set into a solidified material inside the envelope, resembling natural cartilage, wherein the steps listed above generate a filled implant consisting essentially of the flexible envelope and the material inside the envelope, wherein the filled implant is permanently anchored to a bone surface and is medically effective in replacing a damaged segment of cartilage.

12. The method of claim 11, wherein the deformable envelope is made of a flexible synthetic polymer that is biocompatible, non-immunogenic, and not degraded or resorbed by bodily fluids.

13. The method of claim 11, wherein the deformable envelope has an internal surface capable of forming a strong permanent bond with a cold-setting polymeric mixture used for insertion into the flexible envelope during an arthroscopic procedure.

14. The method of claim 11, wherein the deformable envelope has a shape and size designed to replace a cartilage segment in a knee joint selected from the group consisting of a medial femoral condyle and a lateral femoral condyle.

15. The method of claim 11, wherein the deformable envelope has a shape and size designed to replace an entire femoral cartilage surface which includes a medial femoral condyle, a lateral femoral condyle, and a femoral portion of a patello-femoral compartment.

16. The method of claim 11, wherein the deformable envelope has a shape and size designed to replace a cartilage segment in a knee joint selected from the group consisting of a medial tibial plateau and a lateral tibial plateau.

17. The method of claim 11, wherein the deformable envelope has a shape and size designed to replace a cartilage segment in a knee joint which includes both a medial tibial plateau and a lateral tibial plateau.

18. The method of claim 11, wherein the deformable envelope has a shape and size designed to replace a patello-femoral cartilage segment in a knee joint.

19. The method of claim 11, wherein the deformable envelope has a shape and size designed to replace a cartilage segment in a ball-and-socket joint.

20. The method of claim 11, wherein the deformable envelope has a shape and size to replace a portion of an articulating cartilage segment in a mammalian joint.

21. An article of manufacture comprising a sealed package containing a sterile flexible device for replacing a segment of damaged cartilage in a mammalian joint, wherein the sterile flexible device:

(i) is sufficiently flexible to allow it to be arthroscopically inserted into a damaged joint;

(ii) can be restored to a desired size and shape inserted into the damaged joint;

(iii) is designed to be permanently anchored to a bone surface; and (iv) is designed to be filled with a fluidized compound that will set into a solidified material, thereby generating a filled implant consisting of the flexible device and the material inside the flexible device, wherein the filled implant is permanently anchored to a bone surface and is medically effective in replacing a damaged segment of cartilage.

22. The article of manufacture of claim 21, wherein the flexible device is made of a synthetic polymer that is biocompatible, non-immunogenic, and not degraded or resorbed by bodily fluids.

23. The article of manufacture of claim 21, wherein the flexible device has an internal surface capable of forming a strong permanent bond with a cold-setting polymeric mixture used for insertion into the flexible envelope during an arthroscopic procedure.

24. The article of manufacture of claim 21, wherein the flexible device has a shape and size designed to replace a cartilage segment in a knee joint selected from the group consisting of a medial femoral condyle and a lateral femoral condyle.

25. The article of manufacture of claim 21, wherein the flexible device has a shape and size designed to replace an entire femoral cartilage surface which includes a medial femoral condyle, a lateral femoral condyle, and a femoral portion of a patello-femoral compartment.

26. The article of manufacture of claim 21, wherein the flexible device has a shape and size designed to replace a cartilage segment in a knee joint selected from the group consisting of a medial tibial plateau and a lateral tibial plateau.

27. The article of manufacture of claim 21, wherein the flexible device has a shape and size designed to replace a cartilage segment in a knee joint which includes both a medial tibial plateau and a lateral tibial plateau.

28. The article of manufacture of claim 21, wherein the flexible device has a shape and size designed to replace a patello-femoral cartilage segment in a knee joint.

29. The article of manufacture of claim 21, wherein the flexible device has a shape and size designed to replace a cartilage segment in a ball-and-socket joint.

* * * * *